(12) United States Patent
Li et al.

(10) Patent No.: US 6,787,661 B2
(45) Date of Patent: Sep. 7, 2004

(54) TIN-CONTAINING ORGANOLITHIUM COMPOUNDS AND PREPARATION THEREOF

(75) Inventors: Chuanqing Li, Beijing (CN); Aimin Liang, Beijing (CN); Wei Li, Beijing (CN); Liyun Zhao, Beijing (CN); Song Lu, Beijing (CN); Lin Xu, Beijing (CN); Qing Liu, Beijing (CN)

(73) Assignees: China Petroleum and Chemical Corporation, Beijing (CN); Research Institute of Beijing Yanshan, Beijing (CN)

( * ) Notice: Subject to any disclaimer, the term of this patent is extended or adjusted under 35 U.S.C. 154(b) by 49 days.

(21) Appl. No.: 10/167,306

(22) Filed: Jun. 11, 2002

(65) Prior Publication Data

US 2003/0181747 A1 Sep. 25, 2003

(30) Foreign Application Priority Data

Dec. 31, 2001 (CN) .......................... 01145026 A

(51) Int. Cl.$^7$ ............................. C07F 7/22; B01J 31/00; C08F 4/44
(52) U.S. Cl. .................. 556/87; 526/173; 526/176; 526/190; 526/340; 502/152; 260/665 R
(58) Field of Search ....................... 556/87; 260/665 R; 502/152; 526/173, 176, 190, 340

(56) References Cited

U.S. PATENT DOCUMENTS

| 3,426,006 A | 2/1969 | Nützel et al. ............... 260/83.5 |
| 3,886,089 A | 5/1975 | Smith, Jr. .................... 252/429 |
| 5,268,439 A | 12/1993 | Hergenrother et al. ...... 526/340 |
| 5,502,129 A | 3/1996 | Hergenrother et al. ...... 526/176 |
| 5,877,336 A | 3/1999 | Hergenrother et al. ........ 556/87 |
| 6,307,079 B1 * | 10/2001 | Hintze ......................... 556/87 |

FOREIGN PATENT DOCUMENTS

| CN | 1148053 A | 4/1997 |
| CN | 96120500.8 | 2/2001 |
| DE | 150149 | 8/1981 |
| EP | 0743330 A1 | 11/1996 |

OTHER PUBLICATIONS

Polymer, 1981, 22(12), 1724–1728.
Elastomers, 1992, 2(2), 33–37.
Makromol. Chem., 1985, 186, 2017–2024.
J. Organomet. Chem. 1994, 2447 and.
Polymer International, 1991, 24(4), 197–206.

* cited by examiner

Primary Examiner—Porfirio Nazario-Gonzalez
(74) Attorney, Agent, or Firm—Ohlandt, Greeley Ruggiero & Perle

(57) ABSTRACT

The present invention relates to a tin-containing organolithium compound which can be used as anionic polymerization initiators, represented by the following formula (1):

$$R_{4-x}Sn(Y_a-Z_m-Y_b-Li)_x \qquad (1)$$

Wherein R, Z and Y are defined as in the specification; x represents a value of 1 or 2; m represents a value of 0 or 1; a represents a value of 0 to 6, b represents a value of 0 to 6, a+b is from 0 to 6, provided that m=1 when x=1. The tin-containing organolithium compounds according to the present invention can be used as initiators to initiate the polymerization of conjugated dienes and/or monovinyl aromatic hydrocarbons, thereby synthesizing various linear, star or telechelic polymers. The present invention also relates to a method for preparing the tin-containing organolithium compounds according to the present invention.

35 Claims, No Drawings

TIN-CONTAINING ORGANOLITHIUM COMPOUNDS AND PREPARATION THEREOF

BACKGROUND OF THE INVENTION

1. Field of the Invention

The present invention relates to a class of novel tin-containing organolithium compounds which can be used as anionic polymerization initiators and the preparation thereof. More particularly, the present invention relates to novel tin-containing organic monolithium compounds and bislithium compounds which can be used as anionic polymerization initiators and the preparation thereof.

2. Brief Description of Art

When used as anionic polymerization initiators, tin-containing organolithium compounds can produce polymers having, at each molecular chain end, a residual group derived from the initiators, a Sn-containing group, which is advantageous to the reduction in hysteresis of the polymers. U.S. Pat. No. 3,426,006 discloses a process for preparing trialkyltin lithium compounds by reacting 1 mole of stannous chloride with 3 moles of alkyl lithium; U.S. Pat. No. 5,268,439 discloses a process for preparing trialkyltin lithium compounds in one step by reacting a trialkyl tin halide with metallic lithium, but the resultant initiators have a relatively high content of ionic chloride; U.S. Pat. No. 5,502,129 discloses a process for preparing trialkyltin lithium compounds in two steps, aimed at reducing the content of ionic chloride. U.S. Pat. No. 5,877,336 discloses a process for preparing triorganotin lithium compounds by reacting metallic lithium with bis(triorganotin) in dimethyl ether at a temperature of 0 to 65° C. and a pressure of 2 to 20 atms. The tin lithium compounds of the prior art are disadvantageous in that they have relatively poor solubility in solvents conventionally used for polymerization.

Since trialkyltin lithium compounds belong to monolithium compounds and contain only one active Sn—Li bond, such compounds can generally be used to prepare linear polymers and if star polymers are desirable, coupling is necessary.

In terms of preparation of star polymers and simplification of the procedure for preparing block copolymers, organic bislithium compounds have advantages to which conventional monolithium compounds are incomparable. However, none of the adduct of divinyl benzene with monolithium compounds(EP 743 330A1), the adduct of bis(1,1-distyrene) type compounds with monolithium compounds(Quirk R. P., Ma Jing-Jing, Polymer International, 1991, 24(4), 197–206) and oligomeric lithium initiators(DD 150 149) contain, in addition to C, H and Li, other heteroatoms in the molecular chain, and it is well known that the presence of heteroatom Sn in the molecular chain is advantageous for the reduction in hysteresis of polymers.

Chinese Patent Application Publication No. CN 1 148 053A discloses a multifunctional organic alkali metal initiator having a Sn-containing functional group. Such initiators have a functionality of more than 2.5 and thus can only be used to synthesize star polymers.

BRIEF SUMMARY OF THE INVENTION

A general object of the present invention is to provide a class of novel tin-containing organolithium compounds which are free of the disadvantages associated with the prior art and can be used as anionic polymerization initiators. Such compounds contain Sn atom and can be used to synthesize linear, star or telechelic polymers.

A specific object of the present invention is to provide novel tin-containing organic monolithium compounds which can be used as anionic polymerization initiators. Such compounds have good solubility in solvents conventionally used in anionic polymerization and its tin-containing group can retain at the molecular chain end of polymers prepared therewith, thereby reducing hysteresis of such polymers.

Another specific object of the present invention is to provide novel tin-containing organic bislithium compounds which can be used as anionic polymerization initiators. By using such compounds, the procedure for preparing block polymers can be simplified and the resultant polymers have a narrow molecular weight distribution and a high content of tin.

Another general object of the present invention is to provide a method for preparing the tin-containing organolithium compounds in accordance with the present invention.

These and other objects, features and advantages of the present invention will be apparent from the following description.

In its one aspect, the present invention provides a tin-containing organolithium compound which can be used as anionic polymerization initiators, represented by the following formula (1):

$$R_{4-x}Sn(Y_a-Z_m-Y_b-Li)_x \qquad (1)$$

wherein R represents $C_1$–$C_{20}$-alkyl, $C_3$–$C_{20}$-cycloalkyl or $C_6$–$C_{20}$-aryl or substituted aryl; Z represents straight or branched $C_1$–$C_{20}$ divalent hydrocarbon group, $C_6$–$C_{30}$-arylene or substituted arylene; Y represents a group derived from conjugated diene homopolymers, monovinyl aromatic hydrocarbon homopolymers or conjugated diene/monovinyl aromatic hydrocarbon copolymers; x represents a value of 1 or 2; m represents a value of 0 or 1; a represents a value of 0 to 6, b represents a value of 0 to 6, a+b is from 0 to 6, provided that m=1 when x=1.

In its another aspect, the present invention provides a method for preparing the tin-containing organolithium compound of formula (1).

DETAILED DESCRIPTION OF THE INVENTION

The present invention will be described in more detailed as follows.

In the above formula (1), R is preferably $C_1$–$C_{10}$-alkyl, $C_3$–$C_{10}$-cycloalkyl or $C_6$–$C_{10}$-aryl or substituted aryl, wherein alkyl is methyl, ethyl, isopropyl, n-butyl, sec-butyl, n-hexyl, n-octyl, etc.; cycloalkyl may be cyclohexyl; aryl or substituted aryl may be phenyl, o-, m- or p-methylphenyl, etc.; the conjugated diene in the definition of Y is preferably butadiene, isoprene or derivatives thereof, and the monovinyl aromatic hydrocarbon is preferably styrene, α-methylstyrene; Z is preferably straight or branched $C_2$–$C_{10}$ divalent hydrocarbon groups, $C_6$–$C_{20}$ arylene or substituted arylene. The straight or branched $C_2$–$C_{10}$ divalent hydrocarbon group is preferably straight or branched α,ω–$C_2$–$C_{10}$ divalent hydrocarbon group, more preferably α,ω-butylene or α,ω-pentylene; arylene or substituted arylene is preferably those having the following formulae (a), (b), (c), (d), (e) or (f):

(a)

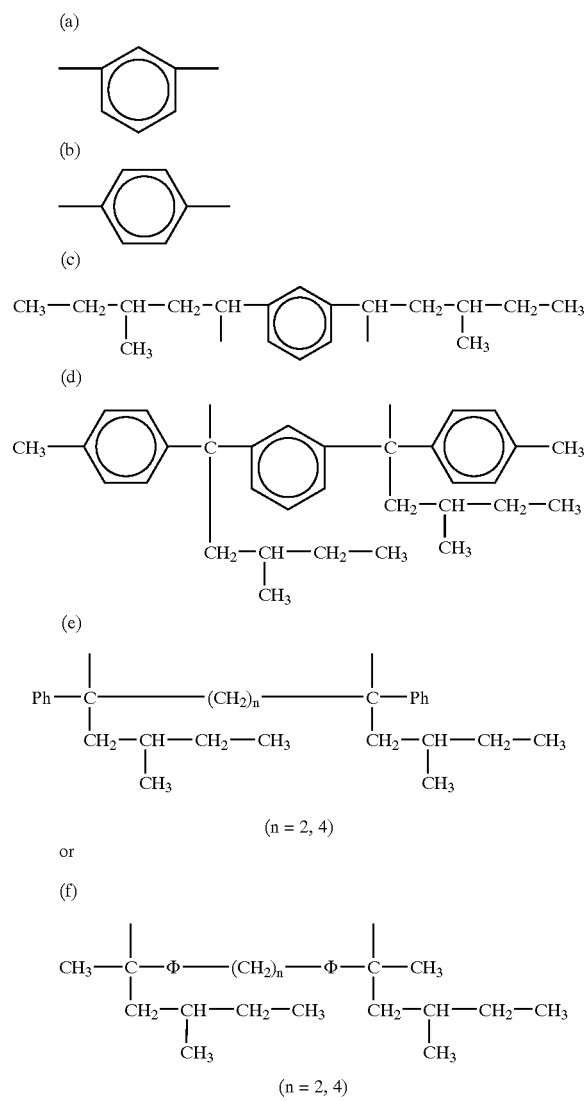

(b)

(c)

(d)

(e)

(n = 2, 4)

or (f)

(n = 2, 4)

The method in accordance with the present invention is slightly varied depending on the parameters x, m, a and b and is described as follows in more details.

I. Preparation of tin-containing organolithium compounds of formula (1) wherein x=1 and m=1

When x=1 and m=1, the tin-containing organolithium compound of formula (1) can be prepared by a method comprising the steps of:

i) preparing a bislithium compound of formula (2):

LiZLi                               (2)

wherein Z is defined as above;

ii) adding a halide of formula (3):

$R_3SnX$                            (3)

wherein R is defined as above; X is halogen selected from fluorine, chlorine, bromine and iodine; and optionally iii) adding and polymerizing conjugated diene monomers, monovinyl aromatic hydrocarbon monomers or mixtures thereof prior to or after step ii), to form a low molecular weight oligomer having an active site.

More particularly, when x=1, m=1, a=0 and b=0, the compound of formula (1) corresponds to the compound of formula (1a):

$R_3SnZLi$                        (1a)

wherein R and Z are defined as above.

The compound of formula (1a) according to the present invention can be prepared by a method comprising the steps of:

i) preparing a bislithium compound of formula (2) as defined above;

ii) adding the halide of formula (3) as defined above and reacting it with the bislithium compound resulting from step i), to obtain the compound of formula (1a).

More particularly, when x=1, m=1, a=0 and b≠0, the compound of formula (1) corresponds to the compound of formula (1b):

$R_3SnZY_bLi$                    (1b)

wherein R, Z, Y and b are defined as above.

The compound of formula (1b) according to the present invention can be prepared by a method comprising the steps of:

i) preparing a bislithium compound of formula (2) as defined above;

ii) reacting the bislithium compound of formula (2) with the halide of formula (3) as defined above, to form the compound of formula (1a) as defined above;

iii) polymerizing conjugated diene monomers, monovinyl aromatic hydrocarbon monomers or mixtures thereof by using the compound of formula (1a), to form the compound of formula (1b).

More particularly, when x=1, m=1, a≠0 and b≠0, the compound of formula (1) corresponds to the compound of formula (1c):

$R_3SnY_aZY_bLi$                (1c)

wherein R, Y, Z, a and b are defined as above.

The compound of formula (1c) according to the present invention can be prepared by a method comprising the steps of:

i) preparing the bislithium compound of formula (2) as defined above; thereafter carrying out step iii), iii) polymerizing conjugated diene monomers, monovinyl aromatic hydrocarbon monomers or mixtures thereof by using the compound of formula (2), to form a compound of formula (2a):

$LiY_aZY_bLi$                   (2a)

wherein Y, Z, a and b are defined as above; finally carrying out step ii)

ii) adding the halide of formula (3) as defined above into the product resulting from step iii) and reacting them, to obtain the compound of formula (1c).

In the step i) of the methods mentioned above, the bislithium compound of formula (2) is an adduct of diene compounds with monolithium compounds, more particularly an adduct of α, ω-$C_2$–$C_{10}$ diene compounds with monolithium compounds, an adduct of divinyl benzene type compounds with monolithium compounds or an adduct of bis(1,1-distyrene) type compounds with monolithium compounds. The bislithium compounds disclosed by the prior art can be used in the present invention, the specific examples thereof being those represented by the following formulae:

(a) Li—(CH$_2$)$_4$—Li (cf. U.S. Pat. No. 3,886,089)
(b) Li—(CH$_2$)$_5$—Li (cf. U.S. Pat. No. 3,886,089)

(c)

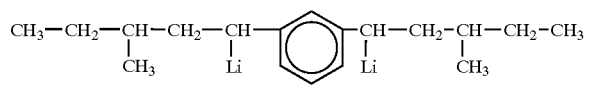

(cf. Friedhelm Bandermann, Hans-Dieter Speikamp and Ludwig Weigel, Makromol. Chem., 1985, 186, 2017–2024);

(d)

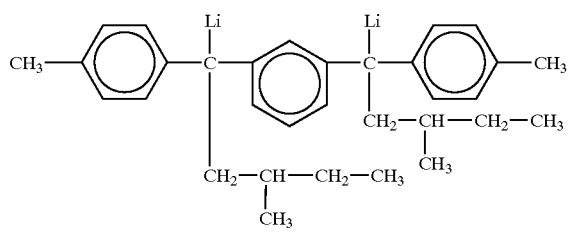

(cf. Shuojian JIANG, Huaibing LIU, Zhong ZHAO, Elastomers, 1992, 2(2), 33–37);

(e)

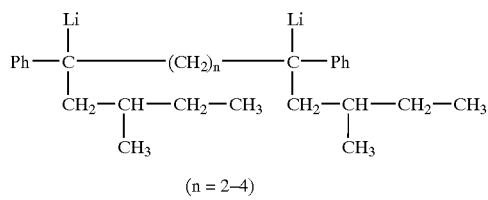

(n = 2–4)

(cf. H. Uytterhoeven, M. Fontanille and P. Sigwalt, Polymer, 1981, 22(12), 1724–1728);

(f)

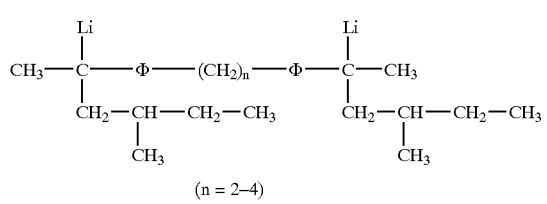

(n = 2–4)

(cf. H. Uytterhoeven, M. Fontanille and P. Sigwalt, Polymer, 1981, 22(12), 1724–1728).

In the step ii) of the methods mentioned above, the reaction of the bislithium compound of formula (2) or (2a) with the halide of formula (3) is preferably carried out in a solvent. The solvent which can be used is ether solvents, such as tetrahydrofuran, dimethyl ether or diethyl ether, or hydrocarbon solvents, such as benzene, toluene, cyclohexane, hexane, pentane, heptane or raffinate oil. These solvents can be used alone or in mixtures of two or more of them. The bislithium compound of formula (2) and the halide of formula (3) are generally reacted at a temperature of 0 to 60° C., preferably 5 to 35° C.; and the bislithium compound of formula (2a) and the halide of formula (3) are generally reacted at a temperature of 0 to 60° C., preferably 5 to 30° C.

In the above methods, the molar ratio of the bislithium compound of formula (2) or (2a) to the halide of formula (3) is 1:1.

In the above methods, the halide of formula (3) is preferably chloride or bromide, more preferably chloride. The halide of formula (3) which can be used in the above methods is tributyl tin chloride, trihexyl tin chloride, trioctyl tin chloride, etc., which are commercially available.

In the step iii) of the methods mentioned above, the polymerization of conjugated diene monomers, monovinyl aromatic hydrocarbon monomers or mixtures thereof in the presence of the compound of formula (1a) or the bislithium compound of formula (2) is preferably carried out in a solvent, and said solvent can be hydrocarbon solvents, for example aromatic hydrocarbon solvents, such as benzene, toluene; aliphatic hydrocarbon solvents, such as cyclohexane, hexane, pentane, heptane, raffinate oil. These solvents can be used alone or in mixtures of two or more of them. The polymerization is carried out at a temperature of 10 to 60° C.

In the above methods, the conjugated diene monomers to be used are preferably butadiene, isoprene or derivatives thereof; the monovinyl aromatic hydrocarbon monomers are preferably styrene, α-methylstyrene.

In the above methods, the ratio of the compound of formula (1a) or the bislithium compound of formula (2) to the monomer used can be varied depending on the designed molecular weight, that is to say, depending on the values of parameters a and b.

In each step of the above method, the reaction is preferably carried out under an atmosphere of inert gas such as argon or nitrogen.

II. Preparation of tin-containing organolithium compounds of formula (1) wherein x=2

II-1. Preparation of tin-containing organolithium compounds of formula (1) wherein a+b=0

More particularly, when x=2, a+b=0 and m=0, the compound of formula (1) corresponds to the compound of formula (1d):

$$R_2SnLi_2 \quad (1d)$$

wherein R is defined as above.

The compound of formula (1d) according to the present invention can be prepared by a method comprising directly reacting a halide of formula (3') with metallic lithium in a solvent:

$$R_2SnX_2 \quad (3')$$

wherein R is defined as above, X is halogen selected from fluorine, chlorine, bromine and iodine, preferably chlorine or bromine.

The halide of formula (3') can be dibutyl tin dichloride, dihexyl tin dichloride, dioctyl tin dichloride, etc. These compounds are all commercially available.

The metallic lithium used in the above reaction is preferably lithium sand having a particle size of 10 to 300 μm.

The above reaction is also preferably carried out under an atmosphere of inert gas such as argon or nitrogen.

The solvent used in the above reaction may be ether solvents, such as tetrahydrofuran, dimethyl ether or diethyl ether, or aromatic hydrocarbon solvents, such as benzene or toluene, preferably tetrahydrofuran. In addition to the above solvents, it is possible to use hydrocarbon solvents, such as hexane or heptane, as diluents in the above reaction, in order to more efficiently remove LiX generated during the reaction.

The above reaction is generally carried out at a temperature of 0 to 70° C., preferably 5 to 35° C.

In the above reaction, the molar ratio of the halide of formula (3') to metallic lithium is 1:4–1:7, preferably 1:4.5–1:6.

More particularly, when x=2, a+b=0 and m=1, the compound of formula (1) corresponds to the compound of formula (1e):

$$R_2Sn(ZLi)_2 \qquad (1e)$$

wherein R and Z are defined as above.

The compound of formula (1e) according to the present invention can be prepared by a method comprising the steps of:

i) preparing the bislithium compound of formula (2) as defined above; and ii) adding the halide of formula (3') as defined above into the product resulting from step i) and reacting them, to form the compound of formula (1e).

The above reaction is also preferably carried out under an atmosphere of inert gas such as argon or nitrogen.

The solvent used for the reaction of the bislithium compound of formula (2) with the halide of formula (3') may be ether solvents, such as tetrahydrofuran, dimethyl ether or diethyl ether, or hydrocarbon solvents, such as benzene, toluene, cyclohexane, hexane, pentane, heptane or raffinate oil. These solvents can be used alone or in mixtures of two or more of them.

The above reaction is generally carried out at a temperature of 0 to 60° C., preferably 5 to 35° C.

In the above reaction, the molar ratio of the bislithium compound of formula (2) to the halide of formula (3') is 2:1.

II-2. Preparation of tin-containing organolithium compound of formula (1) wherein a+b≠0

More particularly, when x=2, a+b≠0 and m=0, the compound of formula (1) corresponds to the compound of formula (1f):

$$R_2Sn(Y_{a+b}\text{—}Li)_2 \qquad (1f)$$

wherein R, Y, a and b are defined as above.

The compound of formula (1f) according to the present invention can be prepared by a method comprising the steps of:

i) polymerizing conjugated diene monomers, monovinyl aromatic hydrocarbon monomers or mixtures of conjugated diene monomers and monovinyl aromatic hydrocarbon monomers in a hydrocarbon solvent by using an aryllithium initiator, to form a low molecular weight oligomer having active sites at both ends of the molecular chain, represented by the formula (2'):

$$Li\text{—}Y_{a+b}\text{—}Li \qquad (2')$$

wherein Y, a and b are defined as above;

ii) adding the halide of formula (3') as defined above and reacting it with the oligomer resulting from step i), to form the compound of formula (1f).

The aryllithium initiator which can be used in the above reaction is a reaction product of fused ring arenes such as naphthalene, α-methylnaphthalene, anthracene, biphenyl, trans-stilbene with metallic lithium, preferably naphthalenyllithium.

The conjugated diene monomers which can be used in the above reaction are butadiene, isoprene or derivatives thereof, etc.; the monovinyl aromatic hydrocarbon monomers are styrene, α-methylstyrene, etc.

The hydrocarbon solvents which can be used in the above method are aromatic hydrocarbon solvents, such as benzene, toluene, etc., aliphatic hydrocarbon solvents, such as cyclohexane, hexane, pentane, heptane, raffinate oil, etc. These solvents can be used alone or in mixtures of two or more of them.

The polymerization is carried out at a temperature of, for example, 10 to 60° C.

The ratio of the aryllithium initiator to the monomer used is varied depending on the designed molecular weight, that is to say, depending on the values of parameters a and b.

The molar ratio of the low molecular weight oligomer of formula (2') to the halide of formula (3') is 2:1.

More particularly, when x=2, a=0, b≠0 and m=1, the compound of formula (1) corresponds to the compound of formula (1g):

$$R_2Sn(Z\text{—}Y_b\text{—}Li)_2 \qquad (1g)$$

wherein R, Z, Y and b are defined as above.

The compound of formula (1g) according to the present invention can be prepared by a method comprising the steps of:

i) preparing the bislithium compound of formula (2) as defined above;

ii) reacting the bislithium compound of formula (2) with the halide of formula (3') as defined above, to obtain the compound of formula (1e) as defined above;

iii) polymerizing conjugated diene monomers, monovinyl aromatic hydrocarbon monomers or mixtures thereof by using the compound of (1e) as the initiator, to form the compound of formula (1g).

The bislithium compound of formula (2) and the halide of formula (3') are preferably reacted in a solvent. Said solvent is, for example, ether solvents, such as tetrahydrofuran, dimethyl ether, diethyl ether, or hydrocarbon solvents, such as benzene, toluene, cyclohexane, hexane, pentane, heptane, raffinate oil. These solvents can be used alone or in mixtures of two of more of them.

The bislithium compound of formula (2) and the halide of formula (3') are preferably reacted at a temperature of 0 to 60° C., more preferably 5 to 35° C.

The molar ratio of the bislithium compound of formula (2) to the halide of formula (3') is 2:1.

The conjugated diene monomers used in the reaction may also be butadiene, isoprene or derivatives thereof; the monovinyl aromatic hydrocarbon monomers may be styrene, α-methylstyrene.

The above reaction is also preferably carried out in a solvent. Said solvent may be hydrocarbon solvents, for example aromatic hydrocarbon solvents, such as benzene, toluene; aliphatic hydrocarbon solvents, such as cyclohexane, hexane, pentane, heptane, raffinate oil. These solvents can be used alone or in mixtures of two or more of them.

The polymerization can be carried out at a temperature of 10 to 60° C.

The ratio of the compound of formula (1e) to the monomer used is varied depending on the designed molecular weight, that is to say, depending on the values of parameters a and b.

More particularly, when x=2, a≠0, b≠0 and m=1, the compound of formula (1) corresponds to the compound of formula (1h):

$$R_2Sn(Y_a\text{—}Z\text{—}Y_b\text{—}Li)_2 \qquad (1h)$$

wherein R, Y, Z, a and b are defined as above.

The compound of formula (1h) according to the present invention can be prepared by a method comprising the steps of:

i) preparing the bislithium compound of formula (2) as defined above, ii) polymerizing conjugated diene monomers, monovinyl aromatic hydrocarbon monomers or mixtures thereof by using the compound of formula (2), to form a low molecular weight oligomer having active sites at both ends of the molecular chain, iii) adding the halide of formula (3') into the resulting product from step ii) and then reacting them, to form the compound of formula (1h).

The bislithium compound of formula (2), the conjugated diene monomers, the monovinyl aromatic hydrocarbon monomers, the solvents and the halide of formula (3') can be selected in a manner similar to the above.

The polymerization is carried out at a temperature of 10 to 60° C.

The oligomer resulting from step ii) and the halide of formula (3') is preferably reacted at a temperature of 0 to 60° C., preferably 5 to 30° C.

The molar ratio of the oligomer resulting from step ii) to the halide of formula (3') is 2:1.

The ratio of the bislithium compound of formula (2) to the monomer used is varied depending on the designed molecular weight, that is to say, depending on the values of parameters a and b.

The tin-containing organolithium compounds according to the present invention can be used as anionic polymerization initiators to initiate the polymerization of conjugated diene monomers and/or monovinyl aromatic hydrocarbon monomers.

EXAMPLES

The present invention is illustrated by the following examples, which however should not be construed as limiting the scope of the present invention.

Examples 1–5

Preparation of $Bu_3SnZLi$

A 100 ml three-necked flask equipped with an electromagnetic stirrer is purged with nitrogen and then is charged with 20 ml of previously prepared bislithium compound LiZLi, followed by dropwise addition of a solution of $Bu_3SnCl$ in THF, with the molar ratio of the bislithium compound LiZLi to $Bu_3SnCl$ being 1:1. The mixture is allowed to react at a temperature of 10° C. for 2 hours. The reaction mixture is then filtered to obtain a clear, pale yellow solution. The active lithium concentration is determined by a double titration method(cf. Gilman and K. F. Cartlidge, J. Organomet. Chem., 1994, 2447). The experimental data is listed in table 1.

Examples 6–25

Preparation of $Bu_3SnZY_bLi$

A 250 ml three-necked flask equipped with an electromagnetic stirrer is purged with argon and then is charged with an amount of previously prepared bislithium compound LiZLi, followed by dropwise addition of an equimolar amount of a solution of $Bu_3SnCl$ in 5 ml THF. The mixture is allowed to react at a temperature of 10° C. for 2 hours. Then to the reaction mixture are charged metered amounts of butadiene and solvent, followed by reaction at a temperature of 20° C. for 1 hour. The active lithium concentration is determined in a manner similar to Example 1. The experimental data is listed in table 2.

Examples 26–45

Preparation of $Bu_3SnY_aZY_bLi$

A 250 ml three-necked flask equipped with an electromagnetic stirrer is purged with argon and then is charged with metered amounts of solvent and monomer, followed by an amount of previously prepared bislithium compound LiZLi. The mixture is then allowed to react at a temperature of 20° C. for 2 hours, followed by dropwise addition of an equimolar amount of a solution of $Bu_3SnCl$ in 5 ml THF. The mixture is allowed to react at a temperature of 20° C. for 2 hours. The active lithium concentration is determined in a manner similar to Example 1. The experimental data is listed in table 3.

Note

In the following Tables 1–11:

1. Bislithium compound 1 is α, ω-dilithiobutane(cf. U.S. Pat. No. 3,886,089); Bislithium compound 2 is 1,1'-(1,3-phenylene)-bis[3-methyl-1-(4-tolyl)pentyl]bislithium(cf. Shuojian JIANG, Huaibing LIU, Zhong ZHAO, Elastomers, 1992, 2(2), 33–37;

Bislithium compound 3 is 1,3-bis(1-lithio-3-methylpentyl)benzene(cf. Friedhelm Bandermann, Hans-Dieter Speikamp and Ludwig Weigel, Makromol. Chem., 1985, 186,2017–2024);

2. Dpn=degree of polymerization

In the following Tables 4–11:

3. Average functionality=(concentration of active lithium×volume of solution)/mole number of $R_2SnCl_2$

TABLE 1

Preparation of $Bu_3SnZLi$

| Ex. | LiZLi | Solvent for LiZLi | Concentration of LiZLi | Amount of THF | Active lithium Concentration |
|---|---|---|---|---|---|
| 1 | Bislithium 1 | Diethyl ether | 1.996 M | 15 ml | 0.47 M |
| 2 | Bislithium 2 | Diethyl ether | 0.47 M | 10 ml | 0.14 M |
| 3 | Bislithium 2 | Toluene | 0.332 M | 10 ml | 0.09 M |
| 4 | Bislithium 3 | Heptane | 0.91 M | 15 ml | 0.22 M |
| 5 | Bislithium 3 | Benzene | 0.842 M | 10 ml | 0.24 M |

TABLE 2

Preparation of $Bu_3SnZY_bLi$

| Ex. | LiZLi | Concentration of LiZLi | Solvent for LiZLi | Amount of solvent for LiZLi | LiZLi | $Bu_3SnCl$ | Butadiene | Oligomerization solvent | Amount of solvent | Dpn | Active lithium Concentration |
|---|---|---|---|---|---|---|---|---|---|---|---|
| 6 | Bislithium 1 | 1.95 M | Diethyl ether | 15 ml | 14.6 mmol | 14.6 mmol | 52.65 mmol | Cyclohexane | 24 ml | 3.6 | 0.333 M |
| 7 | Bislithium 1 | 1.95 M | Diethyl ether | 15 ml | 14.6 mmol | 14.6 mmol | 33.58 mmol | Cyclohexane | 15.4 ml | 2.3 | 0.336 M |
| 8 | Bislithium 1 | 1.95 M | Diethyl ether | 15 ml | 14.6 mmol | 14.6 mmol | 62.78 mmol | Raffinate oil | 28.8 ml | 4.3 | 0.291 M |
| 9 | Bislithium 1 | 1.95 M | Diethyl ether | 15 ml | 14.6 mmol | 14.6 mmol | 37.96 mmol | Raffinate oil | 17.4 ml | 2.6 | 0.372 M |
| 10 | Bislithium 2 | 0.47 M | Diethyl ether | 50 ml | 11.8 mmol | 11.8 mmol | 36.58 mmol | Cyclohexane | 20.8 ml | 3.1 | 0.148 M |
| 11 | Bislithium 2 | 0.47 M | Diethyl ether | 50 ml | 11.8 mmol | 11.8 mmol | 28.32 mmol | Cyclohexane | 16.1 ml | 2.4 | 0.157 M |
| 12 | Bislithium 2 | 0.47 M | Diethyl ether | 50 ml | 11.8 mmol | 11.8 mmol | 47.20 mmol | Raffinate oil | 26.8 ml | 4.0 | 0.140 M |
| 13 | Bislithium 2 | 0.47 M | Diethyl ether | 50 ml | 11.8 mmol | 11.8 mmol | 25.96 mmol | Raffinate oil | 14.5 ml | 2.2 | 0.162 M |
| 14 | Bislithium 2 | 0.332 M | Toluene | 50 ml | 8.3 mmol | 8.3 mmol | 31.54 mmol | Cyclohexane | 25.5 ml | 3.8 | 0.091 M |
| 15 | Bislithium 2 | 0.332 M | Toluene | 50 ml | 8.3 mmol | 8.3 mmol | 17.43 mmol | Cyclohexane | 14.0 ml | 2.1 | 0.112 M |
| 16 | Bislithium 2 | 0.332 M | Toluene | 50 ml | 8.3 mmol | 8.3 mmol | 31.54 mmol | Raffinate oil | 25.5 ml | 3.8 | 0.099 M |
| 17 | Bislithium 2 | 0.332 M | Toluene | 50 ml | 8.3 mmol | 8.3 mmol | 18.26 mmol | Raffinate oil | 14.7 ml | 2.2 | 0.109 M |
| 18 | Bislithium 3 | 0.91 M | Heptane | 30 ml | 13.6 mmol | 13.6 mmol | 53.04 mmol | Cyclohexane | 26.1 ml | 3.9 | 0.203 M |
| 19 | Bislithium 3 | 0.91 M | Heptane | 30 ml | 13.6 mmol | 13.6 mmol | 32.64 mmol | Cyclohexane | 16.1 ml | 2.4 | 0.255 M |
| 20 | Bislithium 3 | 0.91 M | Heptane | 30 ml | 13.6 mmol | 13.6 mmol | 55.76 mmol | Raffinate oil | 27.5 ml | 4.1 | 0.211 M |
| 21 | Bislithium 3 | 0.91 M | Heptane | 30 ml | 13.6 mmol | 13.6 mmol | 36.72 mmol | Raffinate oil | 18.1 ml | 2.7 | 0.246 M |
| 22 | Bislithium 3 | 0.842 M | Benzene | 30 ml | 12.6 mmol | 12.6 mmol | 52.92 mmol | Cyclohexane | 28.1 ml | 4.2 | 0.189 M |
| 23 | Bislithium 3 | 0.842 M | Benzene | 30 ml | 12.6 mmol | 12.6 mmol | 23.94 mmol | Cyclohexane | 12.7 ml | 1.9 | 0.238 M |
| 24 | Bislithium 3 | 0.842 M | Benzene | 30 ml | 12.6 mmol | 12.6 mmol | 46.62 mmol | Raffinate oil | 24.8 ml | 3.7 | 0.204 M |
| 25 | Bislithium 3 | 0.842 M | Benzene | 30 ml | 12.6 mmol | 12.6 mmol | 25.20 mmol | Raffinate oil | 13.4 ml | 2.0 | 0.247 M |

TABLE 3

Preparation of $Bu_3SnY_aZY_bLi$

| Ex. | LiZLi | Concentration of LiZLi | Solvent for LiZLi | Amount of solvent for LiZLi | LiZLi | Butadiene | Oligomerization solvent | Amount of solvent | Dpn | Active lithium concentration |
|---|---|---|---|---|---|---|---|---|---|---|
| 26 | Bislithium 1 | 1.82 M | Diethyl ether | 10 ml | 9.1 mmol | 36.4 mmol | Cyclohexane | 26.8 ml | 4.0 | 0.207 M |
| 27 | Bislithium 1 | 1.82 M | Diethyl ether | 10 ml | 9.1 mmol | 21.84 mmol | Cyclohexane | 16.1 ml | 2.4 | 0.284 M |
| 28 | Bislithium 1 | 1.82 M | Diethyl ether | 10 ml | 9.1 mmol | 35.49 mmol | Raffinate oil | 26.1 ml | 3.9 | 0.209 M |
| 29 | Bislithium 1 | 1.82 M | Diethyl ether | 10 ml | 9.1 mmol | 19.11 mmol | Raffinate oil | 14.1 ml | 2.1 | 0.305 M |
| 30 | Bislithium 2 | 0.47 M | Diethyl ether | 50 ml | 11.8 mmol | 48.38 mmol | Cyclohexane | 27.5 ml | 4.1 | 0.138 M |
| 31 | Bislithium 2 | 0.47 M | Diethyl ether | 50 ml | 11.8 mmol | 24.78 mmol | Cyclohexane | 14.1 ml | 2.1 | 0.163 M |
| 32 | Bislithium 2 | 0.47 M | Diethyl ether | 50 ml | 11.8 mmol | 47.2 mmol | Raffinate oil | 26.8 ml | 4.0 | 0.130 M |
| 33 | Bislithium 2 | 0.47 M | Diethyl ether | 50 ml | 11.8 mmol | 30.68 mmol | Raffinate oil | 17.4 ml | 2.6 | 0.151 M |
| 34 | Bislithium 2 | 0.332 M | Toluene | 50 ml | 8.3 mmol | 32.37 mmol | Cyclohexane | 26.1 ml | 3.9 | 0.100 M |
| 35 | Bislithium 2 | 0.332 M | Toluene | 50 ml | 8.3 mmol | 22.41 mmol | Cyclohexane | 18.1 ml | 2.7 | 0.109 M |
| 36 | Bislithium 2 | 0.332 M | Toluene | 50 ml | 8.3 mmol | 34.86 mmol | Raffinate oil | 28.2 ml | 4.2 | 0.081 M |
| 37 | Bislithium 2 | 0.332 M | Toluene | 50 ml | 8.3 mmol | 19.09 mmol | Raffinate oil | 15.4 ml | 2.3 | 0.103 M |
| 38 | Bislithium 3 | 0.91 M | Heptane | 30 ml | 13.6 mmol | 53.04 mmol | Cyclohexane | 26.1 ml | 3.9 | 0.210 M |
| 39 | Bislithium 3 | 0.91 M | Heptane | 30 ml | 13.6 mmol | 34 mmol | Cyclohexane | 16.8 ml | 2.5 | 0.181 M |
| 40 | Bislithium 3 | 0.91 M | Heptane | 30 ml | 13.6 mmol | 58.48 mmol | Raffinate oil | 28.8 ml | 4.3 | 0.203 M |
| 41 | Bislithium 3 | 0.91 M | Heptane | 30 ml | 13.6 mmol | 31.28 mmol | Raffinate oil | 15.4 ml | 2.3 | 0.259 M |
| 42 | Bislithium 3 | 0.842 M | Benzene | 30 ml | 12.6 mmol | 52.92 mmol | Cyclohexane | 28.2 ml | 4.2 | 0.188 M |
| 43 | Bislithium 3 | 0.842 M | Benzene | 30 ml | 12.6 mmol | 25.2 mmol | Cyclohexane | 13.4 ml | 2.0 | 0.244 M |
| 44 | Bislithium 3 | 0.842 M | Benzene | 30 ml | 12.6 mmol | 51.66 mmol | Raffinate oil | 27.5 ml | 4.1 | 0.185 M |
| 45 | Bislithium 3 | 0.842 M | Benzene | 30 ml | 12.6 mmol | 28.98 mmol | Raffinate oil | 15.4 ml | 2.3 | 0.241 M |

Examples 46 and 47

Preparation of $R_2SnLi_2$

A 250 ml three-necked flask is purged with argon and then is charged with 1.26 g of dispersed lithium sand(cf. Chinese Patent Application No. 96120500.8) and 120 ml dry tetrahydrofuran(THF). Then a solution of 30 mmol $R_2SnX_2$ in 10 ml THF is dropwise added under stirring. The mixture is allowed to react at room temperature for 24 hours and then is heated to a temperature of 45° C. The reaction mixture is filtered to remove the unreacted lithium sand and the by-product LiX, and a clear, pale yellow solution is obtained. The active lithium concentration is determined in a manner similar to Example 1 and then the average functionality is calculated. The results are listed in table 4.

TABLE 4

Preparation of $R_2SnLi_2$

| Ex. | R— | X— | Active lithium concentration(M) | Average functionality |
|---|---|---|---|---|
| 46 | $C_8H_{17}$— | Cl | 0.359 | 1.91 |
| 47 | $C_4H_9$— | Cl | 0.344 | 1.83 |

Examples 48–77

Preparation of $R_2Sn(ZLi)_2$

A 100 ml two-necked flask equipped with an electromagnetic stirrer is purged with nitrogen and then is charged with 20 ml of previously prepared bislithium compound LiZLi, followed by dropwise addition of a solution of $R_2SnCl_2$ in THF, with the molar ratio of the bislithium compound LiZLi to $R_2SnX_2$ being 2:1. The mixture is allowed to react at a temperature of 10° C. for a period of time. The active lithium concentration is determined in a manner similar to Example 1. The results are listed in tables 5 and 6.

previously prepared bislithium compound LiZLi, followed by dropwise addition of a metered amount of a solution of $R_2SnCl_2$ in THF. The resulting mixture is then allowed to react at a temperature of 10° C. for 2 hours. Then metered amounts of butadiene and solvent are added and the resulting mixture is allowed to react at a temperature of 20° C. for 1 hour. The active lithium concentration is determined in a

TABLE 5

Preparation of $R_2Sn(ZLi)_2$(R is $C_8H_{17}$—)

| Ex. | LiZLi | Solvent for LiZLi | Concentration of LiZLi(M) | Amount of THF(ml) | Reaction time(h) | Active lithium concentration (M) | Average functionality |
|---|---|---|---|---|---|---|---|
| 48 | Bislithium 1 | Diethyl ether | 1.996 | 15 | 2 | 0.530 | 1.86 |
| 49 | Bislithium 1 | Diethyl ether | 1.996 | 15 | 3 | 0.529 | 1.86 |
| 50 | Bislithium 1 | Diethyl ether | 1.996 | 15 | 4 | 0.529 | 1.86 |
| 51 | Bislithium 2 | Diethyl ether | 0.47 | 10 | 2 | 0.150 | 1.91 |
| 52 | Bislithium 2 | Diethyl ether | 0.47 | 10 | 3 | 0.152 | 1.93 |
| 53 | Bislithium 2 | Diethyl ether | 0.47 | 10 | 4 | 0.152 | 1.93 |
| 54 | Bislithium 2 | Toluene | 0.332 | 10 | 2 | 0.110 | 1.98 |
| 55 | Bislithium 2 | Toluene | 0.332 | 10 | 3 | 0.108 | 1.94 |
| 56 | Bislithium 2 | Toluene | 0.332 | 10 | 4 | 0.109 | 1.95 |
| 57 | Bislithium 3 | Heptane | 0.91 | 15 | 2 | 0.241 | 1.85 |
| 58 | Bislithium 3 | Heptane | 0.91 | 15 | 3 | 0.244 | 1.88 |
| 59 | Bislithium 3 | Heptane | 0.91 | 15 | 4 | 0.248 | 1.91 |
| 60 | Bislithium 3 | Benzene | 0.842 | 10 | 2 | 0.272 | 1.94 |
| 61 | Bislithium 3 | Benzene | 0.842 | 10 | 3 | 0.271 | 1.93 |
| 62 | Bislithium 3 | Benzene | 0.842 | 10 | 4 | 0.271 | 1.93 |

TABLE 6

Preparation of $R_2Sn(ZLi)_2$(R is $C_4H_9$—)

| Ex. | LiZLi | Solvent for LiZLi | Concentration of LiZLi(M) | Amount of THF(ml) | Reaction time(h) | Active lithium concentration (M) | Average functionality |
|---|---|---|---|---|---|---|---|
| 63 | Bislithium 1 | Diethyl ether | 1.95 | 10 | 2 | 0.606 | 1.66 |
| 64 | Bislithium 1 | Diethyl ether | 1.95 | 10 | 3 | 0.607 | 1.86 |
| 65 | Bislithium 1 | Diethyl ether | 1.95 | 10 | 4 | 0.610 | 1.88 |
| 66 | Bislithium 2 | Diethyl ether | 0.47 | 10 | 2 | 0.149 | 1.90 |
| 67 | Bislithium 2 | Diethyl ether | 0.47 | 10 | 3 | 0.147 | 1.89 |
| 68 | Bislithium 2 | Diethyl ether | 0.47 | 10 | 4 | 0.150 | 1.91 |
| 69 | Bislithium 2 | Toluene | 0.332 | 10 | 2 | 0.104 | 1.87 |
| 70 | Bislithium 2 | Toluene | 0.332 | 10 | 3 | 0.108 | 1.94 |
| 71 | Bislithium 2 | Toluene | 0.332 | 10 | 4 | 0.109 | 1.95 |
| 72 | Bislithium 3 | Heptane | 0.91 | 15 | 2 | 0.243 | 1.87 |
| 73 | Bislithium 3 | Heptane | 0.91 | 15 | 3 | 0.244 | 1.88 |
| 74 | Bislithium 3 | Heptane | 0.91 | 15 | 4 | 0.247 | 1.90 |
| 75 | Bislithium 3 | Benzene | 0.842 | 10 | 2 | 0.267 | 1.90 |
| 76 | Bislithium 3 | Benzene | 0.842 | 10 | 3 | 0.270 | 1.92 |
| 77 | Bislithium 3 | Benzene | 0.842 | 10 | 4 | 0.271 | 1.93 |

Examples 78–93

Preparation of $R_2Sn(Y_{a+b}$—Li$)_2$

A 100 ml polymerization flask equipped with an electromagnetic stirrer is purged with nitrogen and then is charged with metered amounts of monomer and solvent and 12 mmol of naphthalenyllithium initiator. The mixture is allowed to react at a temperature of 20° C. for 1 hour and then to the mixture is added a solution of 6 mmol $R_2SnCl_2$ in 5 ml THF. The resulting mixture is then allowed to react at a temperature of 20° C. for 1 hour. The active lithium concentration is determined in a manner similar to Example 1 and then the average functionality is calculated. The results are listed in table 7.

Examples 94–173

Preparation of $R_2Sn(Z$—$Y_b$—Li$)_2$

A 250 ml two-necked flask equipped with an electromagnetic stirrer is purged with argon and then is charged with manner similar to Example 1 and then the average functionality is calculated. The results are listed in tables 8 and 9.

Examples 174–253

Preparation of $R_2Sn(Y_a$—Z—$Y_b$—Li$)_2$

A 250 ml flask equipped with an electromagnetic stirrer is purged with argon and then is charged with metered amounts of solvent and monomer, followed by previously prepared bislithium compound LiZLi. The resulting mixture is then allowed to react at a temperature of 20° C. for 2 hours. Then a metered amount of a solution of $R_2SnCl_2$ in THF is charged and the resulting mixture is allowed to react at a temperature of 20° C. for 1 hour. The active lithium concentration is determined in a manner similar to Example 1 and then the average functionality is calculated. The results are listed in tables 10 and 11.

TABLE 7

Preparation of $R_2Sn(Y_{a+b}\text{-Li})_2$

| Ex. | R- | Concentration of naphthalenylithium | Solvent | Monomer | Amount of monomer(mmol) | Dpn | Active lithium concentration(M) | Average functionality |
|---|---|---|---|---|---|---|---|---|
| 78 | $C_8H_{17}$— | 1.083 M | Hexane | Butadiene | 48 | 4.0 | 0.224 | 1.72 |
| 79 | $C_8H_{17}$— | 1.083 M | Cyclohexane | Butadiene | 45.6 | 3.8 | 0.229 | 1.68 |
| 80 | $C_8H_{17}$— | 1.083 M | Raffinate oil | Butadiene | 49.2 | 4.1 | 0.217 | 1.70 |
| 81 | $C_8H_{17}$— | 1.083 M | Benzene | Butadiene | 38.4 | 3.2 | 0.277 | 1.81 |
| 82 | $C_8H_{17}$— | 0.92 M | Hexane | Isoprene | 49.2 | 4.1 | 0.216 | 1.73 |
| 83 | $C_8H_{17}$— | 0.92 M | Cyclohexane | Isoprene | 46.8 | 3.9 | 0.200 | 1.67 |
| 84 | $C_8H_{17}$— | 0.92 M | Raffinate oil | Isoprene | 45.6 | 3.8 | 0.218 | 1.71 |
| 85 | $C_8H_{17}$— | 0.92 M | Benzene | Isoprene | 43.2 | 3.6 | 0.256 | 1.79 |
| 86 | $C_4H_9$— | 1.083 M | Hexane | Butadiene | 49.2 | 4.1 | 0.234 | 1.82 |
| 87 | $C_4H_9$— | 1.083 M | Cyclohexane | Butadiene | 46.8 | 3.9 | 0.231 | 1.73 |
| 88 | $C_4H_9$— | 1.083 M | Raffinate oil | Butadiene | 48 | 4.0 | 0.216 | 1.66 |
| 89 | $C_4H_9$— | 1.083 M | Benzene | Butadiene | 44.4 | 3.7 | 0.238 | 1.69 |
| 90 | $C_4H_9$— | 0.92 M | Hexane | Isoprene | 48 | 4.0 | 0.227 | 1.78 |
| 91 | $C_4H_9$— | 0.92 M | Cyclohexane | Isoprene | 40.8 | 3.4 | 0.213 | 1.64 |
| 92 | $C_4H_9$— | 0.92 M | Raffinate oil | Isoprene | 45.6 | 3.8 | 0.214 | 1.68 |
| 93 | $C_4H_9$— | 0.92 M | Benzene | Isoprene | 46.8 | 3.9 | 0.234 | 1.72 |

TABLE 8

Preparation of $R_2Sn(Z\text{—}Y_b\text{—Li})_2$ (R is $C_8H_{17}$—)

| Ex. | LiZLi | Solvent for LiZLi | LiZLi (mmol) | Amount of $R_2SnX_2$ added(mmol) | Monomer | Amount of monomer added (mmol) | Dpn | Polymerization solvent | Active lithium concentration (M) | Average functionality |
|---|---|---|---|---|---|---|---|---|---|---|
| 94 | 1 | Diethyl ether | 14.6 | 7.2 | Butadiene | 40.3 | 2.8 | Cyclohexane | 0.159 | 1.89 |
| 95 | 1 | Diethyl ether | 14.6 | 7.2 | Butadiene | 61.1 | 4.2 | Raffinate oil | 0.136 | 1.80 |
| 96 | 1 | Diethyl ether | 14.6 | 7.2 | Butadiene | 33.6 | 2.3 | Cyclohexane | 0.203 | 1.80 |
| 97 | 1 | Diethyl ether | 14.6 | 7.2 | Butadiene | 33.6 | 2.3 | Raffinate oil | 0.211 | 1.88 |
| 98 | 1 | Diethyl ether | 14.6 | 7.2 | Isoprene | 58.4 | 4.0 | Cyclohexane | 0.184 | 1.89 |
| 99 | 1 | Diethyl ether | 14.6 | 7.2 | Isoprene | 58.4 | 4.0 | Raffinate oil | 0.184 | 1.89 |
| 100 | 1 | Diethyl ether | 14.6 | 7.2 | Isoprene | 38 | 2.6 | Cyclohexane | 0.232 | 1.84 |
| 101 | 1 | Diethyl ether | 14.6 | 7.2 | Isoprene | 42 | 2.9 | Raffinate oil | 0.216 | 1.80 |
| 102 | 2 | Diethyl ether | 11.8 | 5.9 | Butadiene | 47.2 | 4.0 | Cyclohexane | 0.147 | 1.81 |
| 103 | 2 | Diethyl ether | 11.8 | 5.9 | Butadiene | 49.6 | 4.2 | Raffinate oil | 0.145 | 1.86 |
| 104 | 2 | Diethyl ether | 11.8 | 5.9 | Butadiene | 28.3 | 2.4 | Cyclohexane | 0.174 | 1.92 |
| 105 | 2 | Diethyl ether | 11.8 | 5.9 | Butadiene | 27.1 | 2.3 | Raffinate oil | 0.167 | 1.88 |
| 106 | 2 | Diethyl ether | 11.8 | 5.9 | Isoprene | 48.4 | 4.1 | Cyclohexane | 0.114 | 1.86 |
| 107 | 2 | Diethyl ether | 11.8 | 5.9 | Isoprene | 48.4 | 4.1 | Raffinate oil | 0.113 | 1.86 |
| 108 | 2 | Diethyl ether | 11.8 | 5.9 | Isoprene | 24.8 | 2.1 | Cyclohexane | 0.139 | 1.80 |
| 109 | 2 | Diethyl ether | 11.8 | 5.9 | Isoprene | 27.1 | 2.3 | Raffinate oil | 0.137 | 1.82 |
| 110 | 2 | Toluene | 8.3 | 4.15 | Butadiene | 32.4 | 3.9 | Cyclohexane | 0.114 | 1.85 |
| 111 | 2 | Toluene | 8.3 | 4.15 | Butadiene | 33.2 | 4.0 | Raffinateoil | 0.110 | 1.81 |
| 112 | 2 | Toluene | 8.3 | 4.15 | Butadiene | 17.4 | 2.1 | Cyclohexane | 0.128 | 1.91 |
| 113 | 2 | Toluene | 8.3 | 4.15 | Butadiene | 19.9 | 2.4 | Raffinateoil | 0.117 | 1.78 |
| 114 | 2 | Toluene | 8.3 | 4.15 | Isoprene | 33.2 | 4.0 | Cyclohexane | 0.115 | 1.94 |
| 115 | 2 | Toluene | 8.3 | 4.15 | Isoprene | 34.0 | 4.1 | Raffinate oil | 0.113 | 1.89 |
| 116 | 2 | Toluene | 8.3 | 4.15 | Isoprene | 19.1 | 2.3 | Cyclohexane | 0.117 | 1.80 |
| 117 | 2 | Toluene | 8.3 | 4.15 | Isoprene | 18.2 | 2.2 | Raffinate oil | 0.121 | 1.83 |
| 118 | 3 | Heptane | 13.6 | 6.8 | Butadiene | 53 | 3.9 | Cyclohexane | 0.241 | 1.94 |
| 119 | 3 | Heptane | 13.6 | 6.8 | Butadiene | 55.7 | 4.1 | Raffinate oil | 0.225 | 1.89 |
| 120 | 3 | Heptane | 13.6 | 6.8 | Butadiene | 32.6 | 2.4 | Cyclohexane | 0.271 | 1.87 |
| 121 | 3 | Heptane | 13.6 | 6.8 | Butadiene | 27.2 | 2.0 | Raffinate oil | 0.276 | 1.87 |
| 122 | 3 | Heptane | 13.6 | 6.8 | Isoprene | 54.4 | 4.0 | Cyclohexane | 0.216 | 1.91 |
| 123 | 3 | Heptane | 13.6 | 6.8 | Isoprene | 51.6 | 3.8 | Raffinate oil | 0.228 | 1.88 |
| 124 | 3 | Heptane | 13.6 | 6.8 | Isoprene | 32.6 | 2.4 | Cyclohexane | 0.253 | 1.86 |
| 125 | 3 | Heptane | 13.6 | 6.8 | Isoprene | 31.2 | 2.3 | Raffinate oil | 0.256 | 1.81 |
| 126 | 3 | Benzene | 12.6 | 6.3 | Butadiene | 50.4 | 4.0 | Cyclohexane | 0.219 | 1.88 |
| 127 | 3 | Benzene | 12.6 | 6.3 | Butadiene | 49.1 | 3.9 | Raffinate oil | 0.210 | 1.83 |
| 128 | 3 | Benzene | 12.6 | 6.3 | Butadiene | 27.7 | 2.2 | Cyclohexane | 0.259 | 1.85 |
| 129 | 3 | Benzene | 12.6 | 6.3 | Butadiene | 27.7 | 2.2 | Raffinate oil | 0.246 | 1.80 |
| 130 | 3 | Benzene | 12.6 | 6.3 | Isoprene | 51.6 | 4.1 | Cyclohexane | 0.226 | 1.82 |
| 131 | 3 | Benzene | 12.6 | 6.3 | Isoprene | 51.6 | 4.1 | Raffinate oil | 0.223 | 1.81 |
| 132 | 3 | Benzene | 12.6 | 6.3 | Isoprene | 31.5 | 2.5 | Cyclohexane | 0.246 | 1.84 |
| 133 | 3 | Benzene | 12.6 | 6.3 | Isoprene | 29 | 2.3 | Raffinate oil | 0.245 | 1.79 |

TABLE 9

Preparation of $R_2Sn(Z-Y_b-Li)_2$ (R is $C_4H_9-$)

| Ex. | LiZLi | Solvent for LiZLi | Concentration of LiZLi (M) | Amount of LiZLi added (mmol) | Amount of $R_2SnX_2$ added (mmol) | Monomer | Amount of monomer added (mmol) | Dpn | Polymerization solvent | Active lithium concentration (M) | Average functionality |
|---|---|---|---|---|---|---|---|---|---|---|---|
| 134 | 1 | Diethyl ether | 1.95 | 14.6 | 7.2 | Butadiene | 61.1 | 4.2 | Cyclohexane | 0.138 | 1.83 |
| 135 | 1 | Diethyl ether | 1.95 | 14.6 | 7.2 | Butadiene | 58.4 | 4.0 | Raffinate oil | 0.136 | 1.81 |
| 136 | 1 | Diethyl ether | 1.95 | 14.6 | 7.2 | Butadiene | 36.5 | 2.5 | Cyclohexane | 0.200 | 1.87 |
| 137 | 1 | Diethyl ether | 1.95 | 14.6 | 7.2 | Butadiene | 36.5 | 2.5 | Raffinate oil | 0.192 | 1.79 |
| 138 | 1 | Diethyl ether | 1.95 | 14.6 | 7.2 | Isoprene | 58.4 | 4.0 | Cyclohexane | 0.193 | 1.89 |
| 139 | 1 | Diethyl ether | 1.95 | 14.6 | 7.2 | Isoprene | 59.9 | 4.1 | Raffinate oil | 0.177 | 1.85 |
| 140 | 1 | Diethyl ether | 1.95 | 14.6 | 7.2 | Isoprene | 35.0 | 2.4 | Cyclohexane | 0.241 | 1.82 |
| 141 | 1 | Diethyl ether | 1.95 | 14.6 | 7.2 | Isoprene | 33.6 | 2.3 | Raffinate oil | 0.247 | 1.80 |
| 142 | 2 | Diethyl ether | 0.47 | 11.8 | 5.9 | Butadiene | 48.4 | 4.1 | Cyclohexane | 0.155 | 1.92 |
| 143 | 2 | Diethyl ether | 0.47 | 11.8 | 5.9 | Butadiene | 44.8 | 3.8 | Raffinate oil | 0.152 | 1.89 |
| 144 | 2 | Diethyl ether | 0.47 | 11.8 | 5.9 | Butadiene | 24.7 | 2.1 | Cyclohexane | 0.175 | 1.90 |
| 145 | 2 | Diethyl ether | 0.47 | 11.8 | 5.9 | Butadiene | 23.6 | 2.0 | Raffinate oil | 0.168 | 1.82 |
| 146 | 2 | Diethyl ether | 0.47 | 11.8 | 5.9 | Isoprene | 48.4 | 4.1 | Cyclohexane | 0.115 | 1.87 |
| 147 | 2 | Diethyl ether | 0.47 | 11.8 | 5.9 | Isoprene | 47.2 | 4.0 | Raffinate oil | 0.112 | 1.80 |
| 148 | 2 | Diethyl ether | 0.47 | 11.8 | 5.9 | Isoprene | 29.5 | 2.5 | Cyclohexane | 0.132 | 1.79 |
| 149 | 2 | Diethyl ether | 0.47 | 11.8 | 5.9 | Isoprene | 26.0 | 2.2 | Raffinate oil | 0.138 | 1.80 |
| 150 | 2 | Toluene | 0.332 | 8.3 | 4.15 | Butadiene | 31.5 | 3.8 | Cyclohexane | 0.117 | 1.86 |
| 151 | 2 | Toluene | 0.332 | 8.3 | 4.15 | Butadiene | 34.8 | 4.2 | Raffinate oil | 0.112 | 1.86 |
| 152 | 2 | Toluene | 0.332 | 8.3 | 4.15 | Butadiene | 19.1 | 2.3 | Cyclohexane | 0.117 | 1.78 |
| 153 | 2 | Toluene | 0.332 | 8.3 | 4.15 | Butadiene | 19.1 | 2.3 | Raffinate oil | 0.119 | 1.81 |
| 154 | 2 | Toluene | 0.332 | 8.3 | 4.15 | Isoprene | 34.8 | 4.2 | Cyclohexane | 0.104 | 1.79 |
| 155 | 2 | Toluene | 0.332 | 8.3 | 4.15 | Isoprene | 33.2 | 4.0 | Raffinate oil | 0.112 | 1.87 |
| 156 | 2 | Toluene | 0.332 | 8.3 | 4.15 | Isoprene | 16.6 | 2.0 | Cyclohexane | 0.124 | 1.88 |
| 157 | 2 | Toluene | 0.332 | 8.3 | 4.15 | Isoprene | 17.4 | 2.1 | Raffinate oil | 0.121 | 1.84 |
| 158 | 3 | Heptane | 0.91 | 13.6 | 6.8 | Butadiene | 54.4 | 4.0 | Cyclohexane | 0.229 | 1.89 |
| 159 | 3 | Heptane | 0.91 | 13.6 | 6.8 | Butadiene | 55.7 | 4.1 | Raffinate oil | 0.223 | 1.87 |
| 160 | 3 | Heptane | 0.91 | 13.6 | 6.8 | Butadiene | 36.7 | 2.7 | Cyclohexane | 0.266 | 1.92 |
| 161 | 3 | Heptane | 0.91 | 13.6 | 6.8 | Butadiene | 31.2 | 2.3 | Raffinate oil | 0.272 | 1.92 |
| 162 | 3 | Heptane | 0.91 | 13.6 | 6.8 | Isoprene | 51.6 | 3.8 | Cyclohexane | 0.217 | 1.89 |
| 163 | 3 | Heptane | 0.91 | 13.6 | 6.8 | Isoprene | 54.4 | 4.0 | Raffinate oil | 0.217 | 1.82 |
| 164 | 3 | Heptane | 0.91 | 13.6 | 6.8 | Isoprene | 34.0 | 2.5 | Cyclohexane | 0.244 | 1.83 |
| 165 | 3 | Heptane | 0.91 | 13.6 | 6.8 | Isoprene | 28.5 | 2.1 | Raffinate oil | 0.266 | 1.84 |
| 166 | 3 | Benzene | 0.842 | 12.6 | 6.3 | Butadiene | 56.7 | 4.5 | Cyclohexane | 0.217 | 1.93 |
| 167 | 3 | Benzene | 0.842 | 12.6 | 6.3 | Butadiene | 54.2 | 4.3 | Raffinate oil | 0.208 | 1.88 |
| 168 | 3 | Benzene | 0.842 | 12.6 | 6.3 | Butadiene | 27.7 | 2.2 | Cyclohexane | 0.264 | 1.89 |
| 169 | 3 | Benzene | 0.842 | 12.6 | 6.3 | Butadiene | 25.2 | 2.0 | Raffinate oil | 0.260 | 1.86 |
| 170 | 3 | Benzene | 0.842 | 12.6 | 6.3 | Isoprene | 55.4 | 4.4 | Cyclohexane | 0.204 | 1.81 |
| 171 | 3 | Benzene | 0.842 | 12.6 | 6.3 | Isoprene | 56.7 | 4.5 | Raffinate oil | 0.195 | 1.80 |
| 172 | 3 | Benzene | 0.842 | 12.6 | 6.3 | Isoprene | 29.0 | 2.3 | Cyclohexane | 0.252 | 1.84 |
| 173 | 3 | Benzene | 0.842 | 12.6 | 6.3 | Isoprene | 32.7 | 2.6 | Raffinate oil | 0.238 | 1.78 |

TABLE 10

Preparation of $R_2Sn(Y_a-Z-Y_b-Li)_2$ (R is $C_8H_{17}-$)

| Ex. | LiZLi | Solvent for LiZLi | Concentration of LiZLi(M) | Amount of LiZLi added(mmol) | Monomer | Amount of monomer added (mmol) |
|---|---|---|---|---|---|---|
| 174 | 1 | Diethyl ether | 1.82 | 9.1 | Butadiene | 38.9 |
| 175 | 1 | Diethyl ether | 1.82 | 9.1 | Butadiene | 37.3 |
| 176 | 1 | Diethyl ether | 1.82 | 9.1 | Butadiene | 24.5 |
| 177 | 1 | Diethyl ether | 1.82 | 9.1 | Butadiene | 21.8 |
| 178 | 1 | Diethyl ether | 1.82 | 9.1 | Isoprene | 37.3 |
| 179 | 1 | Diethyl ether | 1.82 | 9.1 | Isoprene | 36.4 |
| 180 | 1 | Diethyl ether | 1.82 | 9.1 | Iso rene | 20.9 |
| 181 | 1 | Diethyl ether | 1.82 | 9.1 | Isoprene | 20.9 |
| 182 | 2 | Diethyl ehter | 0.47 | 11.8 | Butadiene | 47.2 |
| 183 | 2 | Diethyl ehter | 0.47 | 11.8 | Butadiene | 42.4 |
| 184 | 2 | Diethyl ehter | 0.47 | 11.8 | Butadiene | 24.8 |
| 185 | 2 | Diethyl ehter | 0.47 | 11.8 | Butadiene | 24.8 |
| 186 | 2 | Diethyl ehter | 0.47 | 11.8 | Isoprene | 49.5 |
| 187 | 2 | Diethyl ehter | 0.47 | 11.8 | Isoprene | 48.3 |
| 188 | 2 | Diethyl ehter | 0.47 | 11.8 | Isoprene | 29.5 |
| 189 | 2 | Diethyl ehter | 0.47 | 11.8 | Isoprene | 27.1 |
| 190 | 2 | Toluene | 0.332 | 8.3 | Butadiene | 32.3 |
| 191 | 2 | Toluene | 0.332 | 8.3 | Butadiene | 31.5 |
| 192 | 2 | Toluene | 0.332 | 8.3 | Butadiene | 16.6 |
| 193 | 2 | Toluene | 0.332 | 8.3 | Butadiene | 18.2 |

TABLE 10-continued

Preparation of $R_2Sn(Y_a\text{---}Z\text{---}Y_b\text{---}Li)_2$ (R is $C_8H_{17}\text{---}$)

| | | | | | | |
|---|---|---|---|---|---|---|
| 194 | 2 | Toluene | 0.332 | 8.3 | Isoprene | 34.0 |
| 195 | 2 | Toluene | 0.332 | 8.3 | Isoprene | 31.5 |
| 196 | 2 | Toluene | 0.332 | 8.3 | Isoprene | 19.1 |
| 197 | 2 | Toluene | 0.332 | 8.3 | Isoprene | 19.1 |
| 198 | 3 | Heptane | 0.91 | 13.6 | Butadiene | 55.7 |
| 199 | 3 | Heptane | 0.91 | 13.6 | Butadiene | 55.7 |
| 200 | 3 | Heptane | 0.91 | 13.6 | Butadiene | 31.2 |
| 201 | 3 | Heptane | 0.91 | 13.6 | Butadiene | 29.9 |
| 202 | 3 | Heptane | 0.91 | 13.6 | Isoprene | 53 |
| 203 | 3 | Heptane | 0.91 | 13.6 | Isoprene | 51.7 |
| 204 | 3 | Heptane | 0.91 | 13.6 | Isoprene | 27.2 |
| 205 | 3 | Heptane | 0.91 | 13.6 | Isoprene | 28.5 |
| 206 | 3 | Benzene | 0.842 | 12.6 | Butadiene | 50.4 |
| 207 | 3 | Benzene | 0.842 | 12.6 | Butadiene | 51.6 |
| 208 | 3 | Benzene | 0.842 | 12.6 | Butadiene | 32.7 |
| 209 | 3 | Benzene | 0.842 | 12.6 | Butadiene | 30.2 |
| 210 | 3 | Benzene | 0.842 | 12.6 | Isoprene | 50.4 |
| 211 | 3 | Benzene | 0.842 | 12.6 | Isoprene | 52.9 |
| 212 | 3 | Benzene | 0.842 | 12.6 | Isoprene | 26.5 |
| 213 | 3 | Benzene | 0.842 | 12.6 | Isoprene | 29 |

| Ex. | Dpn | Polymerization solvent | Amount of $R_2SnX_2$ added(mmol) | Active lithium concentration(M) | Average fuctionality |
|---|---|---|---|---|---|
| 174 | 4.27 | Cyclohexane | 4.55 | 0.124 | 1.94 |
| 175 | 4.1 | Raffinate oil | 4.55 | 0.122 | 1.88 |
| 176 | 2.7 | Cyclohexane | 4.55 | 0.195 | 1.89 |
| 177 | 2.4 | Raffinate oil | 4.55 | 0.210 | 1.90 |
| 178 | 4.1 | Cyclohexane | 4.55 | 0.178 | 1.84 |
| 179 | 4.0 | Raffinate oil | 4.55 | 0.181 | 1.83 |
| 180 | 2.3 | Cyclohexane | 4.55 | 0.258 | 1.87 |
| 181 | 2.3 | Raffinate oil | 4.55 | 0.248 | 1.80 |
| 182 | 4.0 | Cyclohexane | 5.9 | 0.149 | 1.82 |
| 183 | 3.6 | Raffinate oil | 5.9 | 0.148 | 1.81 |
| 184 | 2.1 | Cyclohexane | 5.9 | 0.181 | 1.96 |
| 185 | 2.1 | Raffinate oil | 5.9 | 0.173 | 1.91 |
| 186 | 4.2 | Cyclohexane | 5.9 | 0.115 | 1.89 |
| 187 | 4.1 | Raffinate oil | 5.9 | 0.111 | 1.80 |
| 188 | 2.5 | Cyclohexane | 5.9 | 0.134 | 1.82 |
| 189 | 2.3 | Raffinate oil | 5.9 | 0.139 | 1.84 |
| 190 | 3.9 | Cyclohexane | 4.15 | 0.112 | 1.81 |
| 191 | 3.8 | Raffinate oil | 4.15 | 0.111 | 1.80 |
| 192 | 2.0 | Cyclohexane | 4.15 | 0.128 | 1.92 |
| 193 | 2.2 | Raffinate oil | 4.15 | 0.124 | 1.86 |
| 194 | 4.1 | Cyclohexane | 4.15 | 0.113 | 1.90 |
| 195 | 3.8 | Raffinate oil | 4.15 | 0.116 | 1.90 |
| 196 | 2.3 | Cyclohexane | 4.15 | 0.121 | 1.87 |
| 197 | 2.3 | Raffinate oil | 4.15 | 0.119 | 1.82 |
| 198 | 4.1 | Cyclohexane | 6.8 | 0.227 | 1.87 |
| 199 | 4.1 | Raffinate oil | 6.8 | 0.227 | 1.90 |
| 200 | 2.3 | Cyclohexane | 6.8 | 0.276 | 1.89 |
| 201 | 2.2 | Raffinate oil | 6.8 | 0.267 | 1.85 |
| 202 | 3.9 | Cyclohexane | 6.8 | 0.205 | 1.79 |
| 203 | 3.8 | Raffinate oil | 6.8 | 0.217 | 1.79 |
| 204 | 2.0 | Cyclohexane | 6.8 | 0.260 | 1.82 |
| 205 | 2.1 | Raffinate oil | 6.8 | 0.258 | 1.78 |
| 206 | 4.0 | Cyclohexane | 6.3 | 0.220 | 1.89 |
| 207 | 4.1 | Raffinate oil | 6.3 | 0.206 | 1.83 |
| 208 | 2.6 | Cyclohexane | 6.3 | 0.242 | 1.80 |
| 209 | 2.4 | Raffinate oil | 6.3 | 0.252 | 1.88 |
| 210 | 4.0 | Cyclohexane | 6.3 | 0.205 | 1.78 |
| 211 | 4.2 | Raffinate oil | 6.3 | 0.202 | 1.81 |
| 212 | 2.1 | Cyclohexane | 6.3 | 0.258 | 1.84 |
| 213 | 2.3 | Raffinate oil | 6.3 | 0.249 | 1.82 |

TABLE 11

Preparation of $R_2Sn(Y_a\text{---}Z\text{---}Y_b\text{---}Li)_2$ (R is $C_4H_9\text{---}$)

| Ex. | Solvent for LiZLi | Concentration of LiZLi(M) | Amount of LiZLi added(mmol) | Monomer | Amount of monomer added (mmol) |
|---|---|---|---|---|---|

TABLE 11-continued

| | | Preparation of R₂Sn(Yₐ—Z—Y_b—Li)₂(R is C₄H₉—) | | | | |
|---|---|---|---|---|---|---|
| 214 | 1 | Diethyl ether | 1.82 | 9.1 | Butadiene | 38.9 |
| 215 | 1 | Diethyl ether | 1.82 | 9.1 | Butadiene | 37.3 |
| 216 | 1 | Diethyl ether | 1.82 | 9.1 | Butadiene | 19.1 |
| 217 | 1 | Diethyl ether | 1.82 | 9.1 | Butadiene | 18.2 |
| 218 | 1 | Diethyl ether | 1.82 | 9.1 | Isoprene | 36.4 |
| 219 | 1 | Diethyl ether | 1.82 | 9.1 | Isoprene | 35.5 |
| 220 | 1 | Diethyl ether | 1.82 | 9.1 | Isoprene | 18.2 |
| 221 | 1 | Diethyl ether | 1.82 | 9.1 | Isoprene | 20.0 |
| 222 | 2 | Diethyl ether | 0.47 | 11.8 | Butadiene | 44.8 |
| 223 | 2 | Diethyl ether | 0.47 | 11.8 | Butadiene | 46.0 |
| 224 | 2 | Diethyl ether | 0.47 | 11.8 | Butadiene | 29.5 |
| 225 | 2 | Diethyl ether | 0.47 | 11.8 | Butadiene | 27.1 |
| 226 | 2 | Diethyl ether | 0.47 | 11.8 | Isoprene | 47.2 |
| 227 | 2 | Diethyl ether | 0.47 | 11.8 | Isoprene | 46.0 |
| 228 | 2 | Diethyl ether | 0.47 | 11.8 | Isoprene | 30.7 |
| 229 | 2 | Diethyl ether | 0.47 | 11.8 | Isoprene | 23.6 |
| 230 | 2 | Toluene | 0.332 | 8.3 | Butadiene | 33.2 |
| 231 | 2 | Toluene | 0.332 | 8.3 | Butadiene | 34.8 |
| 232 | 2 | Toluene | 0.332 | 8.3 | Butadiene | 18.3 |
| 233 | 2 | Toluene | 0.332 | 8.3 | Butadiene | 17.4 |
| 234 | 2 | Toluene | 0.332 | 8.3 | Isoprene | 32.4 |
| 235 | 2 | Toluene | 0.332 | 8.3 | Isoprene | 33.2 |
| 236 | 2 | Toluene | 0.332 | 8.3 | Isoprene | 19.9 |
| 237 | 2 | Toluene | 0.332 | 8.3 | Isoprene | 17.4 |
| 238 | 3 | Heptane | 0.91 | 13.6 | Butadiene | 57.1 |
| 239 | 3 | Heptane | 0.91 | 13.6 | Butadiene | 54.4 |
| 240 | 3 | Heptane | 0.91 | 13.6 | Butadiene | 35.3 |
| 241 | 3 | Heptane | 0.91 | 13.6 | Butadiene | 31.2 |
| 242 | 3 | Heptane | 0.91 | 13.6 | Isoprene | 55.7 |
| 243 | 3 | Heptane | 0.91 | 13.6 | Isoprene | 51.6 |
| 244 | 3 | Heptane | 0.91 | 13.6 | Isoprene | 29.9 |
| 245 | 3 | Heptane | 0.91 | 13.6 | Isoprene | 29.9 |
| 246 | 3 | Benzene | 0.842 | 12.6 | Butadiene | 51.7 |
| 247 | 3 | Benzene | 0.842 | 12.6 | Butadiene | 49.1 |
| 248 | 3 | Benzene | 0.842 | 12.6 | Butadiene | 31.5 |
| 249 | 3 | Benzene | 0.842 | 12.6 | Butadiene | 30.2 |
| 250 | 3 | Benzene | 0.842 | 12.6 | Isoprene | 47.9 |
| 251 | 3 | Benzene | 0.842 | 12.6 | Isoprene | 47.9 |
| 252 | 3 | Benzene | 0.842 | 12.6 | Isoprene | 30.2 |
| 253 | 3 | Benzene | 0.842 | 12.6 | Isoprene | 26.4 |

| Ex. | Dpn | Polymerization solvent | Amount of R₂SnX₂ added(mmol) | Active lithium concentration (M) | Fuctionality |
|---|---|---|---|---|---|
| 214 | 4.27 | Cyclohexane | 4.55 | 0.124 | 1.86 |
| 215 | 4.1 | Raffinate oil | 4.55 | 0.145 | 1.86 |
| 216 | 2.1 | Cyclohexane | 4.55 | 0.233 | 1.92 |
| 217 | 2.0 | Raffinate oil | 4.55 | 0.236 | 1.89 |
| 218 | 4.0 | Cyclohexane | 4.55 | 0.182 | 1.85 |
| 219 | 3.9 | Raffinate oil | 4.55 | 0.184 | 1.83 |
| 220 | 2.0 | Cyclohexane | 4.55 | 0.278 | 1.87 |
| 221 | 2.2 | Raffinate oil | 4.55 | 0.257 | 1.79 |
| 222 | 3.8 | Cyclohexane | 5.9 | 0.158 | 1.92 |
| 223 | 3.9 | Raffinate oil | 5.9 | 0.153 | 1.90 |
| 224 | 2.5 | Cyclohexane | 5.9 | 0.168 | 1.88 |
| 225 | 2.3 | Raffinate oil | 5.9 | 0.163 | 1.80 |
| 226 | 4.0 | Cyclohexane | 5.9 | 0.113 | 1.82 |
| 227 | 3.9 | Raffinate oil | 5.9 | 0.117 | 1.87 |
| 228 | 2.6 | Cyclohexane | 5.9 | 0.131 | 1.80 |
| 229 | 2.0 | Raffinate oil | 5.9 | 0.141 | 1.79 |
| 230 | 4.0 | Cyclohexane | 4.15 | 0.118 | 1.89 |
| 231 | 4.2 | Raffinateoil | 4.15 | 0.112 | 1.87 |
| 232 | 2.2 | Cyclohexane | 4.15 | 0.120 | 1.82 |
| 233 | 2.1 | Raffinate oil | 4.15 | 0.122 | 1.83 |
| 234 | 3.9 | Cyclohexane | 4.15 | 0.110 | 1.86 |
| 235 | 4.0 | Raffinate oil | 4.15 | 0.112 | 1.86 |
| 236 | 2.4 | Cyclohexane | 4.15 | 0.117 | 1.84 |
| 237 | 2.1 | Raffinate oil | 4.15 | 0.117 | 1.78 |
| 238 | 4.2 | Cyclohexane | 6.8 | 0.223 | 1.87 |
| 239 | 4.0 | Raffinate oil | 6.8 | 0.227 | 1.89 |
| 240 | 2.6 | Cyclohexane | 6.8 | 0.265 | 1.89 |
| 241 | 2.3 | Raffinate oil | 6.8 | 0.259 | 1.83 |
| 242 | 4.1 | Cyclohexane | 6.8 | 0.207 | 1.86 |
| 243 | 3.8 | Raffinate oil | 6.8 | 0.231 | 1.90 |
| 244 | 2.2 | Cyclohexane | 6.8 | 0.263 | 1.90 |
| 245 | 2.2 | Raffinate oil | 6.8 | 0.267 | 1.87 |

TABLE 11-continued

| | | Preparation of $R_2Sn(Y_a-Z-Y_b-Li)_2$ (R is $C_4H_9-$) | | | |
|---|---|---|---|---|---|
| 246 | 4.1 | Cyclohexane | 6.3 | 0.219 | 1.88 |
| 247 | 3.9 | Raffinate oil | 6.3 | 0.208 | 1.82 |
| 248 | 2.5 | Cyclohexane | 6.3 | 0.250 | 1.84 |
| 249 | 2.4 | Raffinate oil | 6.3 | 0.238 | 1.78 |
| 250 | 3.8 | Cyclohexane | 6.3 | 0.219 | 1.85 |
| 251 | 3.8 | Raffinate oil | 6.3 | 0.212 | 1.83 |
| 252 | 2.4 | Cyclohexane | 6.3 | 0.245 | 1.81 |
| 253 | 2.1 | Raffinate oil | 6.3 | 0.253 | 1.81 |

Examples 254–256

Preparation of Polybutadiene

A 5-liter stainless steel autoclave is purged with nitrogen and then is charged with metered amounts of cyclohexane and THF, followed by a desired amount of butadiene. Afterwards, the autoclave is heated under stirring to reach a temperature of 60° C. and at that temperature, butyllithium is added to remove the impurities reactive to the initiator, followed by a metered amount of a tin-containing organolithium initiator. The reaction mixture is reacted at 60° C. for 3 hours and then a terminating agent, methanol, is added. The content of the autoclave is discharged, and coagulated with steam to remove the solvent and the regulator, then dried to a constant weight. The results are listed in table 12.

TABLE 12

Preparation of polybutadiene

| Ex. | Initiator | Amount of initiator used | Cyclohexane | Butadiene | Amount of terminating agent | Mw | Mn | Mw/Mn |
|---|---|---|---|---|---|---|---|---|
| 254 | Tin-lithium 1 | 2 mmol | 2500 g | 240 g | 5 ml | 263530 | 136544 | 1.93 |
| 255 | Tin-lithium 2 | 2 mmol | 2500 g | 240 g | 5 ml | 239091 | 129108 | 1.85 |
| 256 | Tin-lithium 3 | 2 mmol | 2500 g | 240 g | 5 ml | 248944 | 139395 | 1.79 |

Note:
Tin-lithium 1 is prepared as in Example 1
Tin-lithium 2 is prepared as in Example 6
Tin-lithium 3 is prepared as in Example 26

Examples 257 and 258

Preparation of Polybutadiene

A 5-liter stainless steel autoclave is purged with nitrogen and then is charged with cyclohexane and a metered amount of a regulator, THF, followed by a desired amount of butadiene. Afterwards, the autoclave is heated under stirring to reach a temperature of 60° C. and at that temperature, butyllithium is added to remove the impurities reactive to the initiator, followed by a metered amount of a tin-containing organolithium initiator. The content is allowed to react at 60° C. for 3 hours. Then a terminating agent, methanol, and an antiaging agent, 2,6-di-tert.-butyl-4-methylphenol are added. The content of the autoclave is discharged, and coagulated with steam to remove the solvent and the regulator, then dried to a constant weight. The results are listed in table 13.

TABLE 13

Preparation of Polybutadiene

| Ex. | Initiator | Amount of initiator used, mmol | Cyclohexane, g | Butadiene, g | THF /Li | Amount of terminating agent, ml | Amount of antiaging agent, g | Mw | Mn | Mw/Mn |
|---|---|---|---|---|---|---|---|---|---|---|
| 257 | Tin-lithium 4 | 0.85 | 2000 | 130 | 0 | 10 | 0.7 | 109675 | 96521 | 1.14 |
| 258 | Tin-lithium 5 | 1.4 | 2500 | 220 | 30 | 10 | 1.2 | 242736 | 186958 | 1.3 |

Note:
Tin-lithium 4 is prepared as in Example 63
Tin-lithium 5 is prepared as in Example 48

Example 259

Preparation of Butadiene/styrene Copolymer by Solution Polymerization

A 5-liter stainless steel autoclave is purged with nitrogen and then is charged with a mixture of 70 g of styrene, 2053 g of cyclohexane and 210 g of butadiene. Afterwards, the autoclave is heated in a water bath under stirring to reach a temperature of 50° C. and at that temperature, butyllithium is added to remove the impurities reactive to the initiator, followed by 8.4 mmol of the tin-containing organolithium initiator from Example 63. The reaction mixture is allowed to react for 2 hours and then 10 ml of methanol and 1.6 g of 2,4-di-tert.-butyl-4-methylphenol are added. The content of the autoclave is discharged, and coagulated with steam to remove the solvent and the regulator, then dried to a constant weight. GPC measurements show that the polymer obtained has a weight average molecular weight of 120,000, a number average molecular weight of 110,000, and a molecular weight distribution of 1.09.

Examples 260–262

Preparation of Polybutadiene

A 5-liter stainless steel autoclave is purged with nitrogen and then is charged with cyclohexane and a metered amount of a regulator, THF, followed by a desired amount of butadiene. Afterwards, the autoclave is heated under stirring to reach a temperature of 60° C. and at that temperature, butyllithium is added to remove the impurities reactive to the initiator, followed by a metered amount of a tin-containing organolithium initiator. The reaction mixture is maintained at 60° C. for 3 hours and then a terminating agent, methanol, is added. The content of the autoclave is discharged, and coagulated with steam to remove the solvent and the regulator, then dried to a constant weight. The results are listed in table 14.

TABLE 14

Preparation of polybutadiene

| Ex. | Initiator | Amount of Initiator used, mmol | Cyclohexane, g | Butadiene, g | Amount of terminating agent used, ml | Mw | Mn | Mw/Mn |
|---|---|---|---|---|---|---|---|---|
| 260 | Tin-lithium 6 | 1.5 | 2500 | 240 | 5 | 233932 | 187626 | 1.25 |
| 261 | Tin-lithium 7 | 1.5 | 2500 | 240 | 5 | 130646 | 193287 | 1.18 |
| 262 | Tin-lithium 8 | 1.5 | 2500 | 240 | 5 | 208461 | 174282 | 1.17 |

Note:
Tin-lithium 6 is prepared as in Example 79
Tin-lithium 7 is prepared as in Example 94
Tin-lithium 8 is prepared as in Example 174

While the invention has been described above with reference to specific embodiments thereof, it is apparent that many changes, modifications, and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

What is claimed is:

1. A tin-containing organolithium compound used as anionic polymerization initiators, characterized in that said compound is represented by the following formula (1):

$$R_{4-x}Sn(Y_a\text{—}Z_m\text{—}Y_b\text{—}Li)_x \quad (1)$$

wherein R represents $C_1$—$C_{20}$-alkyl, $C_3$—$C_{20}$-cycloalkyl or $C_6$—$C_{20}$-aryl or substituted aryl; Z represents α, ω-butylene or α, ω-pentylene; Y represents a group derived from conjugated diene homopolymers, monovinyl aromatic hydrocarbon homopolymers or conjugated diene/monovinyl aromatic hydrocarbon copolymers; x represents a value of 1 or 2; m represents a value of 0 or 1; a represents a value of 0 to 6, b represents a value of 0 to 6, and a+b is from 0 to 6, provided that m=1 when x=1.

2. A tin-containing organolithium compound used as anionic polymerization initiators, characterized in that said compound is represented by the following formula (1):

$$R_{4-x}Sn(Y_a\text{—}Z_m\text{—}Y_b\text{—}Li)_x \quad (1)$$

wherein R represents $C_1$–$C_{20}$-alkyl, $C_3$–$C_{20}$-cycloalkyl or $C_6$–$C_{20}$-aryl or substituted aryl; Z represents arylene or substituted arylene of formulae (a), (b), (c), (d), (e) or (f):

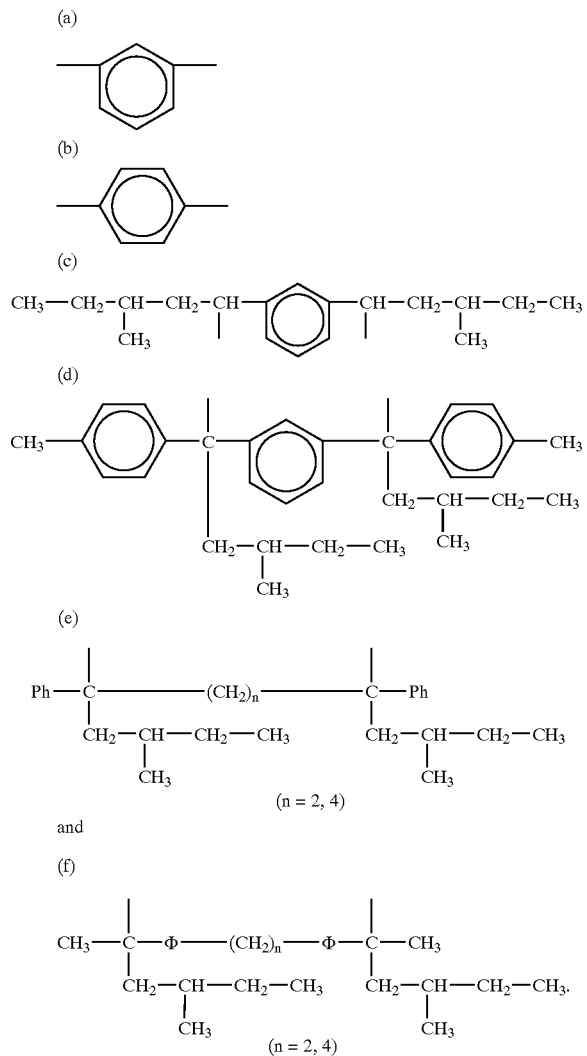

Y represents a group derived from conjugated diene homopolymers, monovinyl aromatic hydrocarbon homopolymers or conjugated diene/monovinyl aromatic hydrocarbon colymers; x represents a value of 1 or 2; m represents a value of 0 or 1; a represents a value of 0 to 6, b represents a value of 0 to 6, and a+b is from 0 to 6, provided that m=1 when x=1.

3. A tin-containing organolithium compound used as anionic polymerization initiators, characterized in that said compound is represented by the following formula (1):

$$R_{4-x}Sn(Y_a-Z_m-Y_b-Li)_x \qquad (1)$$

wherein R represents $C_1$–$C_{20}$-alkyl, $C_3$–$C_{20}$-cycloalkyl or $C_6$–$C_{20}$-aryl or substituted aryl; Z represents straight or branched $C_1$–$C_{20}$ a divalent hydrocarbon group, $C_6$–$C_{30}$-arylene or substituted arylene; Y represents a group derived from conjugated diene homopolymers monovinyl aromatic hydrocarbon homopolymers or conjugated diene/monovinyl aromatic hydrocarbon copolymers; x represents a value of 1 or 2; m represents a value of 0 or 1; a represents a value of 0 to 6, b represents a value of 0 to 6, and a+b is from 0 to 6, provided that m is 1 and a and b cannot be both 0 when x is 1, with said conjugated diene in the definition of Y being butadiene, isoprene or derivatives thereof and the monovinyl aromatic hydrocarbon being styrene or α-methylstyrene.

4. A tin-containing organolithium compound used as anionic polymerization initiators, characterized in that said compound is represented by the following formula (1):

$$R_{4-x}Sn(Y_a-Z_m-Y_b-Li)_x \qquad (1)$$

wherein R represents $C_1$–$C_{20}$-alkyl, $C_3$–$C_{20}$-cycloalkyl or $C_6$–$C_{20}$-aryl or substituted aryl; Z represents straight or branched $C_1$–$C_{20}$ divalent hydrocarbon group, $C_6$–$C_{30}$-arylene or substituted arylene; Y represents a group derived from conjugated diene homopolymers, monovinyl aromatic hydrocarbon homopolymers or conjugated diene/monovinyl aromatic hydrocarbon copolymers; x represents a value of 1; m represents a value of 1; a represents a value of 0, b represents a value of 0 to 6, and a+b is from 0 to 6, provided that b≠0.

5. A tin-containing organolithium compound used as anionic polymerization initiators, characterized in that said compound is represented by the following formula (1):

$$R_{4-x}Sn(Y_a-Z_m-Y_b-Li)_x \qquad (1)$$

wherein R represents $C_1$–$C_{20}$-alkyl, $C_3$–$C_{20}$-cycloalkyl or $C_6$–$C_{20}$-aryl or substituted aryl; Z represents straight or branched $C_1$–$C_{20}$ divalent hydrocarbon group, $C_6$–$C_{30}$-arylene or substituted arylene; Y represents a group derived from conjugated diene homopolymers, monovinyl aromatic hydrocarbon homopolymers or conjugated diene/monovinyl aromatic hydrocarbon copolymers; x represents a value of 1; m represents a value of 1; a represents a value of 0 to 6, b represents a value of 0 to 6, and a+b is from 0 to 6, provided that that a≠0 and b≠0.

6. A tin-containing organolithium compound used as anionic polymerization initiators, characterized in that said compound is represented by the following formula (1):

$$R_{4-x}Sn(Y_a-Z_m-Y_b-Li)_x \qquad (1)$$

wherein R represents $C_1$–$C_{20}$-alkyl, $C_3$–$C_{20}$-cycloalkyl or $C_6$–$C_{20}$-aryl or substituted aryl; Z represents straight or branched $C_1$–$C_{20}$ divalent hydrocarbon group, $C_6$–$C_{30}$-arylene or substituted arylene; Y represents a group derived from conjugated diene homopolymers, monovinyl aromatic hydrocarbon homopolymers or conjugated diene/monovinyl aromatic hydrocarbon copolymers; x represents a value of 2; m represents a value of 0 or 1; and a+b=0.

7. The tin-containing organolithium compound according to claim 6, characterized in that m=0.

8. The tin-containing organolithium compound according to claim 6, characterized in that m=1.

9. A tin-containing organolithium compound used as anionic polymerization initiators, characterized in that said compound is represented by the following formula (1):

$$R_{4-x}Sn(Y_a-Z_m-Y_b-Li)_x \qquad (1)$$

wherein R represents $C_1$–$C_{20}$-alkyl, $C_3$–$C_{20}$-cycloalkyl or $C_6$–$C_{20}$-aryl or substituted aryl; Z represents straight or branched $C_1$–$C_{20}$ divalent hydrocarbon group, $C_6$–$C_{30}$-arylene or substituted arylene; Y represents a group derived from conjugated diene homopolymers, monovinyl aromatic hydrocarbon homopolymers or conjugated diene/monovinyl aromatic hydrocarbon copolymers; x represents a value of 2; m represents a value of 0; and a represents a value of 0 to 6, b represents a value of 0 to 6, and a+b is from 0 to 6, provided that a+b≠0.

10. A tin-containing organolithium compound used as anionic polymerization initiators, characterized in that said compound is represented by the following formula (1):

$$R_{4-x}Sn(Y_a\text{—}Z_m\text{—}Y_b\text{—}Li)_x \quad (1)$$

wherein R represents $C_1$–$C_{20}$-alkyl, $C_3$–$C_{20}$-cycloalkyl or $C_6$–$C_{20}$-aryl or substituted aryl; Z represents straight or branched $C_1$–$C_{20}$ divalent hydrocarbon group, $C_6$–$C_{30}$-arylene or substituted arylene; Y represents a group derived from conjugated diene homopolymers, monovinyl aromatic hydrocarbon homopolymers or conjugated diene/monovinyl aromatic hydrocarbon copolymers; x represents a value of 2; m represents a value of 1; a represents a value of 0, b represents a value of 0 to 6, and a+b is from 0 to 6, provided that b≠0.

11. A tin-containing organolithium compound used as anionic polymerization initiators, characterized in that said compound is represented by the following formula (1):

$$R_{4-x}Sn(Y_a\text{—}Z_m\text{—}Y_b\text{—}Li)_x \quad (1)$$

wherein R represents $C_1$–$C_{20}$-alkyl, $C_3$–$C_{20}$-cycloalkyl or $C_6$–$C_{20}$-aryl or substituted aryl; Z represents straight or branched $C_1$–$C_{20}$ divalent hydrocarbon group, $C_6$–$C_{30}$-arylene or substituted arylene; Y represents a group derived from conjugated diene homopolymers, monovinyl aromatic hydrocarbon homopolymers or conjugated diene/monovinyl aromatic hydrocarbon copolymers; x represents a value of 2; m represents a value of; a represents a value of 0 to 6, b represents a value of 0 to 6, and a+b is from 0 to 6, provided that a≠0 and b≠0.

12. A method for preparing a tin-containing organolithium compound used as anionic polymerization initiators, said compound being represented by the following formula (1):

$$R_{4-x}Sn(Y_a\text{—}Z_m\text{—}Y_b\text{—}Li)_x \quad (1)$$

wherein R represents $C_1$–$C_{20}$-alkyl, $C_3$–$C_{20}$-cycloalkyl or $C_6$–$C_{20}$-aryl or substituted aryl; Z represents straight or branched $C_1$–$C_{20}$ divalent hydrocarbon group, $C_6$–$C_{30}$-arylene or substituted arylene; Y represents a group derived from conjugated diene homopolymers, monovinyl aromatic hydrocarbon homopolymers or conjugated diene/monovinyl aromatic hydrocarbon copolymers; x represents a value of 1; m represents a value of 1; a represents a value of 0 to 6, b represents a value of 0 to 6, and a+b is from 0 to 6, comprising the steps of:

i) preparing a bislithium compound of formula (2):

$$LiZLi \quad (2)$$

wherein Z represents straight or branched $C_1$–$C_{20}$ divalent hydrocarbon group, $C_6$–$C_{30}$-arylene or substituted arylene;

ii) adding a halide of formula (3):

$$R_3SnX \quad (3)$$

wherein R represents $C_1$–$C_{20}$-alkyl, $C_3$–$C_{20}$-cycloalkyl or $C_6$–$C_{20}$-aryl or substituted aryl; X is halogen selected from fluorine, chlorine, bromine and iodine; and optionally iii) adding and polymerizing conjugated diene monomers, monovinyl aromatic hydrocarbon monomers or mixtures thereof, prior to or after step ii), to form a low molecular weight oligomer having an active site.

13. A method for preparing a tin-containing organolithium compound as defined in claim 54, comprising the steps of:

i) preparing the bislithium compound of formula (2)

$$LiZLi \quad (2)$$

wherein Z represents straight or branched $C_1$–$C_{20}$ divalent hydrocarbon group, $C_6$–$C_{30}$-arylene or substituted arylene; and ii) adding the halide of formula (3)

$$R_3SnX \quad (3)$$

wherein R represents $C_1$–$C_{20}$-alkyl, $C_3$–$C_{20}$-cycloalkyl or $C_6$–$C_{20}$-aryl or substituted aryl; and X is halogen selected from fluorine, chlorine, bromine and iodine; and iii) reacting the halide of formula (3) with the bislithium compound resulting from step i), to obtain a compound of formula (1a):

$$R_3SnZLi \quad (1a)$$

wherein Z represents straight or branched $C_1$–$C_{20}$ divalent hydrocarbon group, $C_6$–$C_{30}$-arylene or substituted arylene and R represents $C_1$–$C_{20}$-alkyl, $C_3$–$C_{20}$-cycloalkyl or $C_6$–$C_{20}$-aryl or substituted aryl.

14. The method according to claim 13, further comprising after step ii) the step of polymerizing conjugated diene monomers, monovinyl aromatic hydrocarbon monomers or mixtures thereof by using the compound of formula (1a), to form a compound of formula (1b):

$$R_3SnZY_bLi \quad (1b)$$

wherein Z represents straight or branched $C_1$–$C_{20}$ divalent hydrocarbon group, $C_6$–$C_{30}$-arylene or substituted arylene; R represents $C_1$–$C_{20}$-alkyl, $C_3$–$C_{20}$-cycloalkyl or $C_6$–$C_{20}$-aryl or substituted aryl; Y represents a group derived from conjugated diene homopolymers, monovinyl aromatic hydrocarbon homopolymers or conjugated diene/monovinyl aromatic hydrocarbon copolymers; and b represents a value of 0 to 6.

15. A method for preparing a tin-containing organolithium compound as defined in claim 12, comprising the steps of:

i) preparing the bislithium compound of formula (2)

$$LiZLi \quad (2)$$

wherein Z represents straight or branched $C_1$–$C_{20}$ divalent hydrocarbon group, $C_6$–$C_{30}$-arylene or substituted arylene;

ii) polymerizing conjugated diene monomers, monovinyl aromatic hydrocarbon monomers, or mixtures thereof by using the compound of formula (2), to form a compound of formula (2a):

$$LiY_aZY_bLi \quad (2a)$$

wherein Y represents a group derived from conjugated diene homopolymers, monovinyl aromatic hydrocarbon homopolymers or conjugated diene/monovinyl aromatic hydrocarbon copolymers; Z represents straight or branched $C_1$–$C_{20}$ divalent hydrocarbon group, $C_6$–$C_{30}$-arylene or substituted arylene; a represents a value of 0 to 6; b represents a value of 0 to 6; and a+b is from 0 to 6, provided that that a≠0 and b≠0; and iii) adding the halide of formula (3)

$$R_3SnX \quad (3)$$

wherein R represents $C_1$–$C_{20}$-alkyl, $C_3$–$C_{20}$-cycloalkyl or $C_6$–$C_{20}$-aryl or substituted aryl; X is halogen selected from fluorine, chlorine, bromine and iodine into the product resulting from step ii) and reacting them to obtain a compound of formula (1c):

$$R_3SnY_aZY_bLi \quad (1c)$$

wherein Z represents straight or branched $C_1$–$C_{20}$ divalent hydrocarbon group, $C_6$–$C_{30}$-arylene or substituted arylene; R represents $C_1$–$C_{20}$-alkyl, $C_3$–$C_{20}$-cycloalkyl or $C_6$–$C_{20}$-aryl or substituted aryl; Y represents a group derived from conjugated diene homopolymers, monovinyl aromatic hydrocarbon homopolymers or conjugated diene/monovinyl aromatic hydrocarbon copolymers; a represents a value of 0 to 6; b represents a value of 0 to 6; and a+b is from 0 to 6, provided that a≠0 and b≠0.

16. The method according to claim 12, characterized in that the molar ratio of the bislithium compound of formula (2) to the halide of formula (3) is 1:1.

17. The method according to claim 12, characterized in that X in formula (3) is chlorine or bromine.

18. The method according to claim 17, characterized in that X in formula (3) is chlorine.

19. The method according to claim 12, characterized in that the bislithium compound of formula (2) is an adduct of diene compounds with monolithium compounds.

20. A method for preparing the tin-containing organolithium compound as claimed in claim 7, characterized in that a halide of formula (3') is reacted directly with metallic lithium:

$$R_2SnX_2 \quad (3')$$

wherein R represents $C_1$–$C_{20}$-alkyl, $C_3$–$C_{20}$-cycloalkyl or $C_6$–$C_{20}$-aryl or substituted aryl and X is halogen selected from fluorine, chlorine, bromine and iodine.

21. The method according to claim 20, characterized in that the molar ratio of the halide of formula (3') to metallic lithium is from 1:4 to 1:7.

22. The method according to claim 20, characterized in that metallic lithium is lithium sand having a particle size of 10 μm to 300 μm.

23. The method according to claim 20, characterized in that X in formula (3') is chlorine or bromine.

24. A method for preparing the tin-containing organolithium compound as claimed in claim 8, comprising the steps of:
i) preparing the bislithium compound of formula (2)

$$LiZLi \quad (2)$$

wherein Z represents straight or branched $C_1$–$C_{20}$ divalent hydrocarbon group, $C_6$–$C_{30}$-arylene or substituted arylene;
ii) adding the halide of formula (3')

$$R_2SnX_2 \quad (3')$$

wherein R represents $C_1$–$C_{20}$-alkyl, $C_3$–$C_{20}$-cycloalkyl or $C_6$–$C_{20}$-aryl or substituted aryl and X is halogen selected from fluorine, chlorine, bromine and iodine into the product resulting from step i); and
iii) reacting the bislithium compound of formula (2) with the halide of formula (3').

25. The method according to claim 24, characterized in that the molar ratio of the bislithium compound of formula (2) to the halide of formula (3') is 2:1.

26. A method for preparing the tin-containing organolithium compound as claimed in claim 9, comprising the steps of:
i) polymerizing conjugated diene monomers, monovinyl aromatic hydrocarbon monomers or mixtures of conjugated diene monomers and monovinyl aromatic hydrocarbon monomers in a hydrocarbon solvent by using an aryllithium initiator, to form a low molecular weight oligomer having active sites at both ends of the molecular chain, represented by the formula (2'):

$$Li\text{—}Y_{a+b}\text{—}Li \quad (2')$$

wherein Y represents a group derived from conjugated diene homopolymers, monovinyl aromatic hydrocarbon homopolymers or conjugated diene/monovinyl aromatic hydrocarbon copolymers; a represents a value of 0 to 6; b represents a value of 0 to 6; and a+b is from 0 to 6, provided that a+b≠0;
ii) adding the halide of formula (3')

$$R_2SnX_2 \quad (3')$$

wherein R represents $C_1$–$C_{20}$-alkyl, $C_3$–$C_{20}$-cycloalkyl or $C_6$–$C_{20}$-aryl or substituted aryl and X is halogen selected from fluorine, chlorine, bromine and iodine; and
iii) reacting the halide of formula (3') with the oligomer resulting from step i).

27. The method according to claim 26, characterized in that the aryllithium initiator is the reaction product of fused ring arenes selected from naphthalene, α-methylnaphthalene, anthracene, biphenyl and trans-stilbene with metallic lithium.

28. The method according to claim 27, characterized in that the aryllithium initiator is naphthanlenyllithium.

29. The method according to claim 26, characterized in that the molar ratio of the low molecular weight oligomer of formula (2') to the halide of formula (3') is 2:1.

30. A method for preparing the tin-containing organolithium compound as claimed in claim 10, comprising the steps of:
i) preparing the bislithium compound of formula (2)

$$LiZLi \quad (2)$$

wherein Z represents straight or branched $C_1$–$C_{20}$ divalent hydrocarbon group, $C_6$–$C_{30}$-arylene or substituted arylene;
ii) reacting the bislithium compound of formula (2) with the halide of formula (3')

$$R_2SnX_2 \quad (3')$$

wherein R represents $C_1$–$C_{20}$-alkyl, $C_3$–$C_{20}$-cycloalkyl or $C_6$–$C_{20}$-aryl or substituted aryl and X is halogen selected from fluorine, chlorine, bromine and iodine, to obtain a compound of formula (1e)

$$R_2Sn(Z\text{—}Li)_2 \quad (1e)$$

wherein R represents $C_1$–$C_{20}$-alkyl, $C_3$–$C_{20}$-cycloalkyl or $C_6$–$C_{20}$-aryl or substituted aryl and Z represents straight or branched $C_1$–$C_{20}$ divalent hydrocarbon group, $C_6$–$C_{30}$-arylene or substituted arylene; and
iii) polymerizing conjugated diene monomers, monovinyl aromatic hydrocarbon monomers or mixtures thereof by using the compound of formula (1e) as the initiator.

31. A method for preparing the tin-containing organolithium compound as claimed in claim 11, comprising the steps of:
i) preparing the bislithium compound of formula (2)

$$LiZLi \quad (2)$$

wherein Z represents straight or branched $C_1$–$C_{20}$ divalent hydrocarbon group, $C_6$–$C_{30}$-arylene or substituted arylene;
ii) polymerizing conjugated diene monomers, monovinyl aromatic hydrocarbon monomers or mixtures thereof by using the compound of formula (2) as the initiator, forming a low molecular weight oligomer having active sites at both ends of the molecular chain;

iii) adding the halide of formula (3')

$$R_2SnX_2 \quad (3')$$

wherein R represents $C_1$–$C_{20}$-alkyl, $C_3$–$C_{20}$-cycloalkyl or $C_6$–$C_{20}$-aryl or substituted aryl and X is halogen selected from fluorine, chlorine, bromine and iodine, into the resulting product from step ii); and iv) reacting the product from step ii) with the halide of formula (3').

32. The method according to claim 12, characterized in that the bislithium compound of formula (2) is an adduct of $\alpha,\omega$-$C_2$–$C_{10}$ diene compounds with monolithium compounds, an adduct of divinyl benzene type compounds with monolithium compounds or an adduct of bis(1,1-distyrene) type compounds with monolithium compounds.

33. The method according to claim 31, characterized in that the molar ratio of the low molecular weight oligomer obtained by using the bislithium compound of formula (2) as the initiator to the halide of formula (3') is 2:1.

34. The method according to claim 20, characterized in that said halide of formula (3') is dibutyl tin dichloride, dihexyl tin dichloride, or dioctyl tin dichloride.

35. The method according to claim 26, characterized in that said conjugated diene monome is butadiene, isoprene or derivatives thereof and said monovinyl aromatic hydrocarbon monomer is styrene, $\alpha$-methylstyrene.

* * * * *